| United States Patent [19] | [11] Patent Number: 4,877,872 |
|---|---|
| Morgan et al. | [45] Date of Patent: Oct. 31, 1989 |

[54] PRODUCTION AND USE OF DIMERS OF HEMATOPOROPHYRIN, PURPURINS, CHLORINES AND PURPURIN- AND CHLORIN-COMPLEXES

[75] Inventors: Alan R. Morgan; Steven H. Selman; Greta M. Garbo; Rick W. Keck, all of Toledo, Ohio

[73] Assignee: The University of Toledo, Toledo, Ohio

[21] Appl. No.: 877,770

[22] Filed: Jun. 24, 1986

[51] Int. Cl.⁴ ............................................. A61K 31/40
[52] U.S. Cl. .................................. 540/145; 530/389; 534/15; 534/16; 514/185; 514/410; 436/548; 935/107; 935/108; 935/110
[58] Field of Search ................. 540/145; 514/185, 410; 935/107, 108, 110; 530/389; 436/548; 534/15, 16

[56] References Cited

U.S. PATENT DOCUMENTS

| 4,444,744 | 4/1984 | Goldenberg | 424/9 |
|---|---|---|---|
| 4,649,151 | 3/1987 | Dougherty | 514/410 |
| 4,656,186 | 4/1987 | Bommer | 514/410 |
| 4,675,338 | 6/1987 | Bommer | 514/410 |

FOREIGN PATENT DOCUMENTS 0142732 5/1985 European Pat. Off. .

OTHER PUBLICATIONS

Kessel—I Cancer Research 46, 2248–2251, (1986).
Kessel—II, Chemical Abstracts 106:46579f, (1987).
Angew. Chem. Internat.Edit./vol. 14, No. 5, pp. 361 et seq., 1975, Journal of the Chemical Society, Perkin Transactions I, pp. 1660, et seq., 1979.

*Primary Examiner*—Robert J. Warden
*Assistant Examiner*—Robert Benson
*Attorney, Agent, or Firm*—Willian Brinks Olds Hofer Gilson & Lione

[57] ABSTRACT

Dimers which are either esters or amides of (1) a purpurin, a chlorin or a metal complex and (2) hematoporphyrin or a purpurin, a chlorin or a metal complex are disclosed. The purpines and their metal complexes have the structures of FIGS. 1, 7, 14–18, 29–38, 44–48 and 54–58 of the attached drawings. The chlorins and their metal complexes have the formulas of FIGS. 2, 8, 19–28, 39–43 or 49–53 of the attached drawings. Solutions of the purpurins, chlorins and metal complexes which are physiologically acceptable for intravenous administration are also disclosed, as are emulsions or suspensions of the solutions. The solvent for the solutions can be a product of the reaction of ethylene oxide with castor oil. A method for detecting and treating tumors in human and animal patients is also disclosed. The method comprises administering one of the dimers to the patient. For detection, the patient is then illuminated with ultra violet light; for treatment, the patient is illuminated with visible light of a wavelength at which the purpurin, chlorin or complex administered shows an absorption peak or with X rays or other ionizing radiation.

Dimers of purpurins, chlorine and metal complexes which can be detected by nuclear magnetic resonance or by an instrument that detects ionizing radiation are also disclosed. The purpurins, chlorins and coplexers of these dimers have the formula of one of FIGS. 1, 2, 7, 8, or 14–58 and a structure which is enriched in an atom that can be detected by nuclear magnetic resonance, e.g., C-13 or N-15, or by an instrument that detects ionizing radiation, e.g., C-14, I-131 or Tc-99m.

3 Claims, 12 Drawing Sheets

PRODUCTION AND USE OF DIMERS OF HEMATOPOROPHYRIN, PURPURINS, CHLORINES AND PURPURIN- AND CHLORIN-COMPLEXES

BACKGROUND OF THE INVENTION

1. Field of the invention

This invention relates to the production and use of dimers of a family of purpurins, a family of chlorins and metal complexes of the purpurins and chlorins, with hematoporphyrin or with purpurins, chlorins or complexes, and to compositions containing the dimers. The purpurins have a reduced pyrrole ring and an unsaturated isocyclic ring fused to a pyrrole ring; the unsaturated isocyclic ring of the purpurins corresponds with a saturated ring in the chlorins. The dimers are esters or amides of the purpurins, chlorins or complexes with hematoporphyrin or another purpurin, chlorin or complex. The chlorin dimers are useful as green dyes. The chlorin, purpurin and complex dimers are useful in the detection and treatment of tumors; after they have been administered systemically, e.g., intravenously, they localize preferentially in a tumor. After they have been administered, and have localized in a tumor, their presence can be detected by illumination with ultra violet light, which causes them to fluoresce. The chlorin, purpurin and complex dimers of the invention can also be used to treat tumors; after they have been administered and have localized, irradiation with light of a wave length at which they show an absorbance peak causes a reaction which damages or destroys the tumor where they have localized. The compositions containing the purpurin, chlorin and complex dimers are solutions thereof in an organic liquid that is physiologically acceptable for intravenous or topical administration and emulsions or suspensions of such solutions and water or saline or other solutions.

2. The Prior Art

Four purpurins having an unsaturated isocyclic ring fused to a reduced pyrrole ring are known to be reported in the prior art, a communication to the editor by Woodward et al., JACS, Vol. 82, pp. 3800 et seq., 1960, where they are disclosed as intermediates in the synthesis of chlorophyll, and journal articles by Witte et al., Angew, Chem. Internat. Edit./Vol. 14, No. 5, pp. 361 et seq., 1975, and Arnold et al., Journal of the Chemical Society, Perkin Transactions I, pp. 1660 et seq., 1979. No utility for purpurins is suggested by either Witte et al. or Arnold et al. In addition, European patent application EP142,732 is said (C.A. 103: 123271S) to disclose certain chlorins of a different family and that they accumulate preferentially in the cancer cells of hampsters infected with pancreatic cancer.

Purpurins and chlorins are similar in structure to porphyrins. One porphyrin, called protoporphyrin IX, can be separated from blood. Hematoporphyrin can be produced from protoporphyrin IX; a chemical mixture derived from hematoporphyrin, called hematoporphyrin derivative, and often abreviated "HpD", can be administered intravenously and used in the manner described above for the detection and treatment of tumors. The exact composition of HpD, however, is not known; in fact, it is a mixture of many different prophyrins and related compounds (see, for example, *Porphyrin Photosensitization*, edited by David Kassel and Thomas J. Dougherty, Plenum Press, New York and London, 1983, pp. 3-13).

A published European patent application is understood to disclose certain dimers where two phlorin, porphyrin, chlorin or the like moieties are linked to one another through an ether group, and the use of those dimers in the manner described above for the detection and treatment of tumors. Finally, *Porphyrin Photosensitization*, edited by David Kassel, Plenum Press, New York and London, 1985, pp. 213-228, discloses dimers which are esters of certain chlorins with hematoporphyrin; the dimers are said to localize as described above, even though the chlorins from which they are produced do not.

Figure 1:
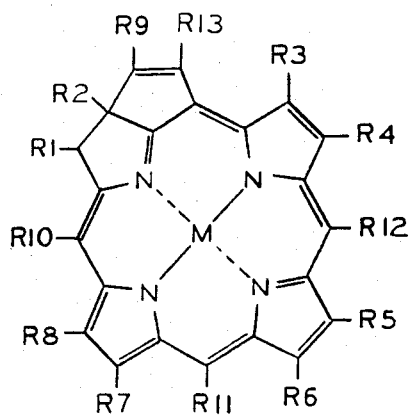
FIG. 1 is a structural formula for metal complexes of a family of purpurins from which dimers according to the instant invention can be produced; in these complexes, an unsaturated isocyclic ring is fused to a reduced pyrrole ring.

FIGS. 49-53 are structural formulas for metal complexes of chlorins having the formulas of FIGS 39-43; dimers according to the instant invention can be produced from these complexes.

FIGS. 54-58 are structural formulas for metal complexes purpurins having the formulas of FIGS. 34-38; dimers according to the instant invention can be produced from these complexes.

BRIEF DESCRIPTION OF THE INVENTION

The instant invention, in one aspect, is a dimer of a purpurin or of a purpurin metal complex having the structure of any of FIGS. 1, 7, 14-18, 29-38, 44-48 or 54-58, or of a chlorin or of a chlorin metal complex having the structure of any of FIGS. 2, 8, 19-28, 39-43, or 49-53 of the attached drawings with hematoporphyrin, or with another purpurin, purpurin metal complex, chlorin or chlorin metal complex. The dimer is either an ester or an amide in which two moieties, one from a purpurin, a chlorin or a metal complex and one from hematoporphyrin, a purpurin, a chlorin or a metal complex are linked through a carbonyl of an ester linkage or through a carbonyl of an amide linkage. In the indicated drawing figures, M is a metal, for example, Ag, Al, Ce, Co, Cr, Cu, Dy, Er, Eu, Fe, Ga, Gd, Hf, Ho, In, La, Lu, Mn, Mo, Nd, Ni, Pb, Pd, Pr, Pt, Rh, Sb, Sc, Sm, Sn, Tb, Th, Tc-99m, Ti, Tl, Tm, U, V, Y, Yb, Zn or Zr and each of $R_1$ through $R_{16}$ is:

H or CHO, a primary or secondary alkyl group having from 1 to 4 carbon atoms, an alkylene group having from 2 to 4 carbon atoms, a group having the formula $R_2N(R_3)_2$ where $R_2$ is a bivalent aliphatic hydrocarbon radical having from 1 to 4 carbon atoms, wherein any carbon to carbon bond is either a single or a double bond, and not more than one is a double bond; $R_3$ is hydrogen or an alkyl group having from 1 to 2 carbon atoms and the two $R_3$ groups can be the same or different, a group having the formula $R_2N(R_4)_3^+$ where $R_2$ is a bivalent aliphatic hydrocarbon radical having from 1 to 4 carbon atoms, wherein any carbon to carbon bond is either a single or a double bond, and not more than one is a double bond; and $R_4$ is an alkyl group having from 1 to 2 carbon atoms and the three $R_4$ groups can be the same or different, a group having the formula $R_2OH$ where $R_2$ is a bivalent aliphatic hydrocarbon radical having from 1 to 4 carbon atoms, wherein any carbon to carbon bond is either a single or a double bond, and not more than one is a double bond, an amino acid moiety which is attached to the purpurin or chlorin moiety through a carbonyl which is a part of an amide produced by reaction between an amino acid and the purpurin or chlorin, or $CO_2R'$, $CH_2CO_2R'$ or $CH_2CH_2CO_2R'$ where R' is H, or a primary or secondary alkyl group having from one to four carbon atoms.

In addition, in the purpurins and purpurin metal complexes of FIGS. 1, 7, 9-13, 14-18, 29-38, 44-48 and 54-58 and in the chlorins and chlorin metal complexes of FIGS. 2, 8, 24-28, 39-43, 44-48 and 49-53 $R_1$ can be a bivalent aliphatic hydrocarbon radical having from 2 to 4 carbon atoms wherein both of the valences of the radical are attached to the same carbon atom thereof and to a carbon atom of the purpurin, chlorin, or metal complex, and in the purpurins and purpurin metal complexes of FIGS. 29-33 and of FIGS. 44-48, both $R_1$ and $R_2$ can be bivalent aliphatic hydrocarbon radicals having from 2 to 4 carbon atoms wherein both of the valences of the radical are attached to the same carbon atom thereof and to a carbon atom of the purpurin or metal complex.

In another aspect, the invention is a method for detecting and treating tumors which comprises administering an effective amount of a dimer according to the invention to a human or animal patient, and irradiating the relevant region of the patient with ultra violet or with visible light of a wavelength at which the purpurin or chlorin has an absorbance peak.

In still another aspect, the invention is a dimer composed of two moieties, one a purpurin, a chlorin or a metal complex which has a structure that is enriched in an atom that can be detected by nuclear magnetic resonance and the other hematoporphyrin or another purpurin, chlorin or metal complex. The atom in which the structure is enriched can be, for example, n-15 or C-13. The purpurin, chlorin or complex can have the formula of any of FIGS. 1, 2, 7, 8 or 14-58 where M and $R_1$ through $R_{16}$ have the meanings set forth above.

In yet another aspect the invention is a method for the treatment of non-malignant lesions, e.g., of the vagina or bladder, or such cutaneous lesions as are involved in psoriasis; the method involves the topical application of a dimer composed of two moieties, one a chlorin, a purpurin or a complex, and the other hematoporphyrin or another purpurin, chlorin or complex and illumination of the area in question. The topical application can be of a solution, e.g., in DMSO or ethanol. The purpurin, chlorin or complex can have the formula of any of FIGS. 1, 2, 7, 8 or 14-58 where M and $R_1$ through $R_{16}$ have the meanings set forth above.

In a further aspect, the invention is a method for treating human or animal patients which involves administering a dimer composed of two moieties, one a chlorin, purpurin or metal complex and the other hematoporphyrin or another chlorin, purpurin or metal complex, and then treating the affected region with X rays. There are indications that the chlorins and the like are X ray sensitizers which increase the therapeutic ratio of X rays.

In another aspect, the invention is a dimer composed of two moieties, one a chlorin, a purpurin or a complex and the other hematoporphyrin or another chlorin, purpurin or complex wherein the dimer includes a chlorin, purpurin or complex coupled to a monoclonal antibody moiety. An amine group of the monoclonal antibody can be reacted with a carboxyl group of the dimer or it can b reacted with a carboxyl group of the hematoporphyrin or of the chlorin or the like before the dimer is produced; as a consequence, the dimer and the monoclonal antibody are coupled through a carbonyl which is a part of an amide produced by reaction between the monoclonal antibody and the hematoporphyrin, purpurin, chlorin or complex. The monoclonal antibody binds to a tumor, in this way increasing the selectivity of the dimer coupled thereto. The purpurin, chlorin or complex can have the formula of any of FIGS. 1, 2, 7, 8, or 14-58 where M is a metal, at least one of $R_1$ through $R_{16}$ is:

a monoclonal antibody which is an amino acid moiety attached to the purpurin or chlorin moiety through a carbonyl which is a part of an amide produced by reaction between the monoclonal antibody and the purpurin or chlorin, and each of the others of R1 through R16 is:

H or CHO, a primary or secondary alkyl group having from 1 to 4 carbon atoms, an alkylene group having from 2 to 4 carbon atoms, a group having the formula $R_2N(R_3)_2$ where $R_2$ is bivalent aliphatic hydrocarbon radical having from 1 to 4 carbon atoms, wherein any carbon to carbon bond is either a single or a double bond, and not more than one is a double bond; $R_3$ is hydrogen or an alkyl group having from 1 to 2 carbon atoms and the two $R_3$ groups can be the same or different, a group having the formula $R_2N(R_4)_2{}^+$ where $R_2$ is a bivalent aliphatic hydrocarbon radical having from 1 to 4 carbon atoms, wherein any carbon to carbon bond is either a single or a double bond, and not more than one is a double bond; and $R_4$ is an alkyl group having from 1 to 2 carbon atoms and the three $R_4$ groups can be the same or different, a group having the formula $R_2OH$ were $R_2$ is a bivalent aliphatic hydrocarbon radical having from 1 to 4 carbon atoms, wherein any carbon to carbon bond is either a single or a double bond, and not more than one is a double bond, $CO_2R'$, $CH_2CO_2R'$ or $CH_2CH_2CO_2R'$ where $R'$ is H, or a primary or secondary alkyl group having from one to four carbon atoms.

In addition, in the purpurins and purpurin metal complexes of FIGS. 9–13, 14–18, 29–38, 44–48 and 54–58 and in the chlorins and chlorin metal complexes of FIGS. 24–28, 39–43, 44–48 and 49–53 R1 can be a bivalent aliphatic hydrocarbon radical having from 2 to 4 carbon atoms wherein both of the valences of the radical are attached to the same carbon atom thereof and to a carbon atom of the purpurin, chlorin, or metal complex, and in the purpurins and purpurin metal complexes of FIGS. 29–33 and of FIGS. 44–48, both R1 and R2 can be bivalent aliphatic hydrocarbon radicals having from 2 to 4 carbon atoms wherein both of the valences of the radical are attached to the same carbon atom thereof and to a carbon atom of the purpurin or metal complex.

In still another aspect the invention is a dimer composed of two moieties, one a purpurin, a chlorin or a metal complex and the other hematoporphyrin or a purpurin, chlorin or metal complex; the dimer includes a purpurin, chlorin or metal complex which has a structure that is enriched in a radioactive atom that can be detected by an instrument for measuring ionizing radiation. The atom can be, for example, C-14, Tc-99M, or I-131. The purpurin, chlorin or complex can have the formula of any of FIGS. 1, 2, 7, 8, or 14–58 where M and R1 through R16 have the meanings set forth above.

OBJECTS OF THE INVENTION

It is, therefore, an object of the invention to provide a new composition which is a dimer of a purpurin or a purpurin complex having the structure of any of FIGS. 1, 7, 14–18, 29–38, 44–48 or 54–58 or of a chlorin or a chlorin complex having the structure of any of FIGS. 2, 8, 19–28, 39–43 or 49–53 of the attached drawings with hematoporphyrin, or with another purpurin, purpurin metal complex, chlorin or chlorin metal complex.

It is a further object to provide a solution in an organic liquid, and an aqueous emulsion of the solution, of a dimer composed of two moieties, one a purpurin or purpurin complex having the structure of any of FIGS. 1, 7, 14–18, 29–38, 44–48 or 54–58 or of a chlorin or chlorin complex having the structure of any of FIGS. 2, 8, 19–28, 39–43 or 49–53 of the attached drawings, and the other hematoporphyrin or another purpurin, chlorin or metal complex.

It is a further object to provide a dimer composed of two moieties, one a purpurin, a chlorin or a metal complex and the other hematoporphyrin or another purpurin, chlorin or metal complex, and having a structure that is enriched in an atom that can be detected by nuclear magnetic resonance.

It is still another object of the invention to provide a dimer which is coupled to a monoclonal antibody and is composed of two moieties, one a purpurin, chlorin or metal complex and the other hematoporphyrin or another purpurin, chlorin or metal complex.

It is a still further object to provide a method for the treatment of non-malignant lesions or of such cutaneous lesions as are involved in psoriasis by the topical application of a solution in DMSO or the like of a dimer, followed by illumination of the affected region, where the dimer is composed of two moieties, one a purpurin, chlorin or metal complex and the other hematoporphyrin or another purpurin, chlorin or metal complex.

It is yet another object of the invention to provide a method for detecting and treating tumors which comprises administering a dimer to a human or animal patient, followed by illumination of the region affected with ultraviolet, with visible light or with X rays, scanning of the region affected by nuclear magnetic resonance, or scanning of the region affected with an instrument that measures ionizing radiation where the dimer is composed of two moieties, one a purpurin, chlorin or metal complex and the other hematoporphyrin or another purpurin, chlorin or metal complex.

It is a still further object of the invention to provide a dimer that is enriched in an atom that can be detected by an instrument that measures ionizing radiation where the dimer is composed of two moieties, one a chlorin, purpurin or metal complex and the other hematoporphyrin or another purpurin, chlorin or metal complex.

DESCRIPTION OF THE PREFERRED EMBODIMENTS

Examples 1 through 13 hereof set forth the best mode presently contemplated by the inventors, insofar as this invention is directed to dimers and their production, where the dimers are composed of two moieties, one a purpurin, chlorin, or metal complex and the other hematoporphyrin or another purpurin, chlorin or metal complex. The in vivo test procedures describe the best mode insofar as this invention is directed to solutions of dimers in an organic liquid and to the production of such solutions, where the dimers are composed of two moieties, one a purpurin, chlorin or complex and the other hematoporphyrin or another purpurin, chlorin or metal complex. The in vitro and in vivo test procedures describe the best mode insofar as the invention is directed to a method for the detection and treatment of tumors, which method involves the use of dimers composed of two moieties, one a purpurin, chlorin or metal complex and the other hematoporphyrin or another purpurin, chlorin or metal complex.

In the examples, and elsewhere herein, the term "percent v/v" means percent by volume; the term "percent w/w" means percent by weight; the term "alkyl group" is used in its ordinary sense to mean a monovalent, saturated, aliphatic hydrocarbon radical; the term "alkylene group" is used in its ordinary sense to mean a monovalent, aliphatic hydrocarbon radical which has one carbon to carbon double bond and in which any other carbon to carbon bond is a single bond; all temperatures are in °C.; and the following abbreviations have the meanings indicated: mg=milligram or milligrams; g=gram or grams; kg=kilogram or kilograms; ml=milliliter or milliliters; cm=centimeter or centimeters; ε=molar absorptivity; and mw=milliwatts.

EXAMPLE 1

The production of four novel dimers according to the invention (hereafter Dimer I, Dimer II, Dimer III and Dimer IV) is described in this example. The dimers are composed of a hematoporphyrin moiety chemically bonded to a moiety of a purpurin (hereafter "Purpurin I"), the production of which is also described. The hematoporphyrin moiety of the dimers has the structure of FIG. 3 of the attached drawings where R, R10, R11 and R12 are H, R1, R3, R5 and R8 are $CH_3$, one of R2 and R4 is $CHOHCH_3$ while the other is a bivalent group having the structure $OCHCH_3$, and R6 and R7 are $CH_2CH_2CO_2H$, while the Purpurin I moiety of the dimers has the structure of FIG. 34 of the attached drawings where R1-R5, R7 and R8 are $CH_2CH_3$, one of R9 and R15 is a bivalent carbonyl group while the other is $CO_2H$, and R10, R12, R13 and R16 are H. The bivalent carbonyl group, R9 or R15 of the purpurin, is bonded to the purpurin and to the oxygen of the bivalent group having the structure $OCHCH_3$, R2 or R4 of the hematoporphyrin; the carbon of the latter bivalent group which is bonded to oxygen is also bonded to the hematoporphyrin.

Figure 4:
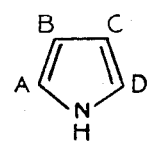
FIG. 4 is a structural formula for pyrroles from which prophyrins having the structure of FIG. 3 can be produced.

The synthesis involves the production of several pyrroles which are identified and assigned trivial names in the following table:

| Compound | Structure (referring to attached drawings) | |
|---|---|---|
| Pyrrole I | FIG. 4, where | A is $CO_2CH_2C_6H_5$ |
| | | B is $CH_2CH_3$ |
| | | C is $CO_2CH_2CH_3$ |
| | | D is $CH_3$ |
| Pyrrole II | FIG. 4, where | A is $CO_2CH_2C_6H_5$ |
| | | B is $CH_2CH_3$ |
| | | C is $CO_2CH_2CH_3$ |
| | | D is $CH_2OCOCH_3$ |
| Pyrrole III | FIG. 4, where | A is $CO_2CH_2C_6H_5$ |
| | | B is $CH_2CH_3$ |
| | | C is $COCH_3$ |
| | | D is $CH_3$ |
| Pyrrole IV | FIG. 4, where | A is $CO_2CH_2C_6H_5$ |
| | | B is $CH_2CH_3$ |
| | | C is $CH_2CH_3$ |
| | | D is $CH_3$ |
| Pyrrole V | FIG. 4, where | A is $CO_2CH_2C_6H_5$ |
| | | B is $CH_2CH_3$ |
| | | C is $CH_2CH_3$ |
| | | D is H |
| Pyrrole VI | FIG. 4, where | A is $CO_2CH_2C_6H_5$ |
| | | B is $CH_2CH_3$ |
| | | C is $CH_2CH_3$ |
| | | D is $CH_2OCOCH_3$ |

Figure 5:
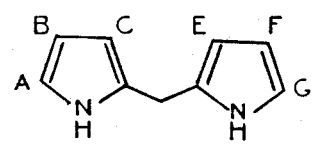
FIG. 5 is a structural formula for dipyrromethanes which are intermediates for the production of prophyrins from pyrroles.

The synthesis also involves the production of several dipyrromethanes which are identified and assigned trivial names in the following table:

| Compound | Structure (referring to attached drawings) | |
|---|---|---|
| Dipyrromethane I | FIG. 5, where | A is $CO_2CH_2C_6H_5$ |
| | | B is $CH_2CH_3$ |
| | | C is $CO_2CH_2CH_3$ |
| | | E is $CH_2CH_3$ |
| | | F is $CH_2CH_3$ |
| | | G is $CO_2CH_2C_6H_5$ |
| Dipyrromethane II | FIG. 5, where | A is $CO_2CH_2C_6H_5$ |
| | | B is $CH_2CH_3$ |
| | | C is $CH_2CH_3$ |
| | | E is $CH_2CH_3$ |
| | | F is $CH_2CH_3$ |
| | | G is $CO_2CH_2C_6H_5$ |
| Dipyrromethane III | FIG. 5, where | A is CHO |
| | | B is $CH_2CH_3$ |
| | | C is $CH_2CH_3$ |
| | | E is $CH_2CH_3$ |
| | | F is $CH_2CH_3$ |
| | | G is CHO |

Figure 3:
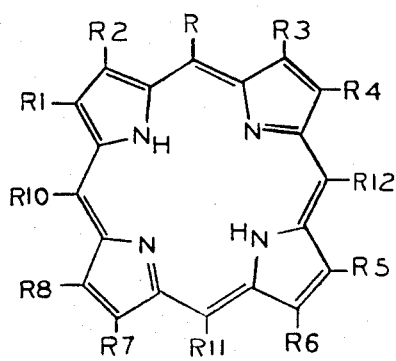
FIG. 3 is a structural formula for a family of prophyrins which can be used to produce purpurins having the formula of FIG. 7.
Figure 6:
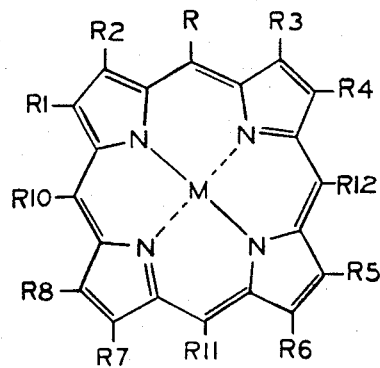
FIG. 6 is a structural formula for metal complexes of prophyrins having the formula of FIG. 3.

The synthesis also involves the production of two porphyrins and six porphyrin complexes, all of which are identified and given trivial names in the following table:

| Compound | Structure (referring to attached drawings) | |
|---|---|---|
| Porphyrin I | FIG. 3, where | R and R10-R12 are hydrogen |
| | | R1 and R3-R8 are $CH_2CH_3$ |
| | | R2 is $CO_2H$ |
| Porphyrin Complex II | FIG. 6, where | R and R10-R12 are hydrogen |
| | | R1 and R3-R8 are $CH_2CH_3$ |
| | | R2 is $CO_2H$ |
| | | M is Ni |
| Porphyrin Complex III | FIG. 6, where | R is CHO |
| | | R1 and R3-R8 are $CH_2CH_3$ |
| | | R2 is $CO_2H$ |
| | | R10-R12 are H |
| | | M is Ni |
| Porphyrin Complex IV | FIG. 6, where | R, R11 and R12 are H |
| | | R1 and R3-R8 are $CH_2CH_3$ |
| | | R2 is $CO_2H$ |
| | | R10 is CHO |
| | | M is Ni |
| Porphyrin Complex V | FIG. 6, where | R, R10 and R12 are H |
| | | R1 and R3-R8 are $CH_2CH_3$ |
| | | R2 is $CO_2H$ |
| | | R11 is CHO |
| | | M is Ni |
| Porphyrin Complex VI | FIG. 6, where | R, R10 and R11 are hydrogen |
| | | R1 and R3-R8 are $CH_2CH_3$ |
| | | R2 is $CO_2H$ |
| | | R12 is CHO |
| | | M is Ni |
| Porphyrin Complex VII | FIG. 6, where | R, R10 and R12 are H |
| | | R1 and R3-R8 are $CH_2CH_3$ |
| | | R2 is $CO_2H$ |
| | | R11 is $CH=CHCO_2CH_2CH_3$ |
| | | M is Ni |
| Porphyrin VIII | FIG. 3, where | R, R10 and R12 are hydrogen |
| | | R1 and R3-R8 are $CH_2CH_3$ |
| | | R2 is $CO_2H$ |
| | | R11 is $CH=CHCO_2CH_2CH_3$ |

Figure 9:
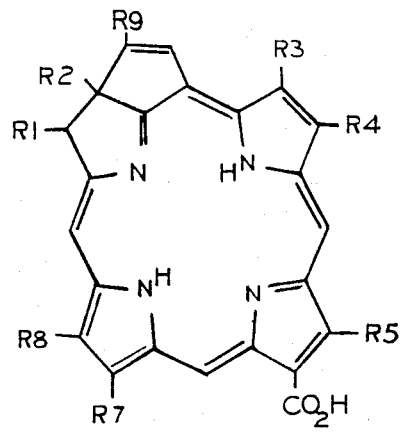
FIGS. 9-13 are structural formulas for five different carboxy purpurins, each of which can be used in the synthesis of different position isomers of purpurins having the structure of FIG. 7 or to produce dimers according to the instant invention.
Figure 13:
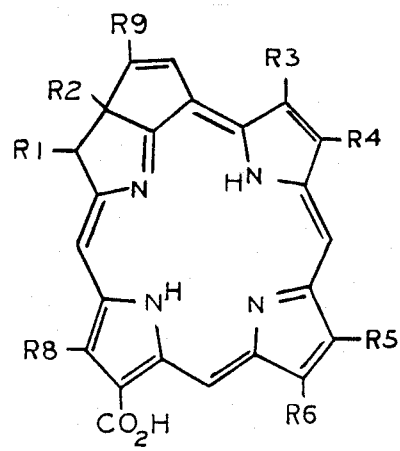
Figure 34:
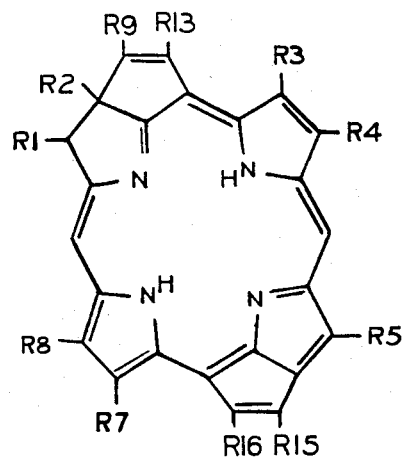
FIGS. 34-38 are structural formulas for purpurins having two isocyclic rings fused to pyrrole rings; dimers according to the instant invention can be produced from these purpurins.

Purpurin I and other purpurins that are produced in the course of the synthesis thereof are identified and the other purpurins are assigned trivial names in the following table:

| Compound | Structure (referring to attached drawings) | |
|---|---|---|
| Purpurin I | FIG. 34: | R1-R5, R7 and R8 are $CH_2CH_3$ |
| | | R9 is $CO_2CH_2CH_3$ |
| | | R13 and R16 are H |
| | | R15 is $CO_2CH_2CH_3$ |
| Purpurin II | FIG. 9: | R1-R5, R7 and R8 are $CH_2CH_3$ |
| | | R9 is $CO_2CH_2CH_3$ |
| Purpurin III | FIG. 13: | R1-R6 and R8 are $CH_2CH_3$ |
| | | R9 is $CO_2CH_2CH_3$ |

Figure 14:
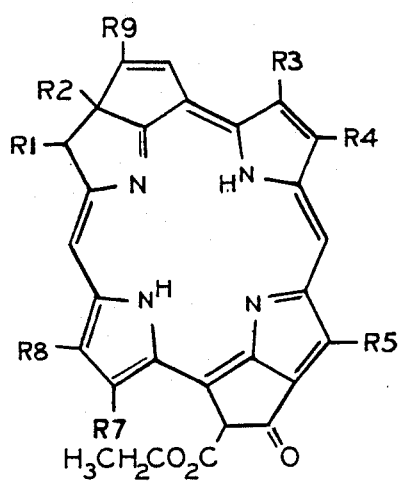
FIGS. 14-18, FIGS. 19-23, and FIGS. 24-28 are structural formulas for intermediates in the synthesis of purpurin position isomers having the formulas of FIGS. 29-33 from the carboxy purpurins having the formulas of FIGS. 9-13; dimers according to the instant invention can be produced from the intermediates of FIGS. 14-28 and from the purpurins of FIGS. 29-33.

| Compound | Structure (referring to attached drawings) |
|---|---|
| Purpurin IV | FIG. 14: R1–R5, R7 and R8 are CH$_2$CH$_3$<br>R9 is CO$_2$CH$_2$CH$_3$ |
| Purpurin V | FIG. 7: R1–R5, R7 and R8 are CH$_2$CH$_3$<br>R6 is (O=C)CH$_2$CO$_2$CH$_3$<br>R9 is CO$_2$CH$_2$CH$_3$<br>R10–R13 are hydrogen |

PRODUCTION OF PYRROLE I

Pyrrole I is produced from a saturated aqueous solution containing one gram equivalent of sodium nitrite, a 5 percent w/w solution in glacial acetic acid containing one gram equivalent of benzyl propionylacetate, a suspension in glacial acetic acid of one gram equivalent of ethyl acetoacetate and four gram equivalents of zinc dust. The sodium nitrite solution is added dropwise, with stirring, to the benzyl propionylacetate solution at a rate sufficiently slow that the temperature of the solution that is formed does not exceed 20°. After the resulting solution stands at room temperature of about 22° for thirty minutes, the zinc dust is added in increments to the ethyl acetoacetate suspension at such a rate that the exotheric reaction which occurs heats the slurry to about 65°; the foregoing solution is then added dropwise, with stirring, to the ethyl acetoacetate/zinc slurry. The reaction mixture is maintained at 65° during the addition and for an hour after completion of the addition of the sodium nitrite/benzyl propionylacetate solution; stirring is continued during the additional hour. The hot solution is then separated from the zinc by decantation. The Pyrrole I is precipitated by pouring the hot solution into ice water, and is recovered by filtration and air dried.

PRODUCTION OF PYRROLE II

Pyrrole II is produced from 6 g lead tetra-acetate and a solution of 4 g Pyrrole I in 2 ml acetic anhydride and 100 ml glacial acetic acid. The lead tetra-acetate is added to the Pyrrole I solution and dissolved by warming the resulting reaction mixture on a steam bath for about 10 minutes. The solution so formed is stirred at room temperature of about 22° for 16 hours. Dropwise additions of ice are then made to precipitate the Pyrrole II, which is recovered from the reaction mixture by filtration and washed with distilled water.

PRODUCTION OF PYRROLE III

Pyrrole III is produced from a saturated aqueous solution containing one gram equivalent of sodium nitrite, a 5 percent w/w solution in glacial acetic acid containing one gram equivalent of benzyl propionylacetate, a suspension in glacial acetic acid of one gram equivalent of 2,4-pentanedione and four gram equivalents of zinc dust. The sodium nitrite solution is added dropwise, with stirring, to the benzyl propionyl-acetate solution at a rate sufficiently slow that the temperature of the solution that is formed does not exceed 20°. After the resulting solution stands at room temperature of about 22° for thirty minutes, the zinc dust is added in increments to the 2,4-pentanedione suspension at such a rate that the exothermic reaction which occurs heats the slurry to about 65°; the foregoing solution is then added dropwise, with stirring, to the 2,4-pentanedions/-zinc slurry. The reaction mixture is maintained at 65° during the addition and for an hour after completion of the addition of the sodium nitrite/benzyl propionyl-acetate solution; stirring is continued during the additional hour. The hot solution is then separated from the zinc by decantation. The Pyrrole III is precipitated by pouring the hot solution into ice water, and is recovered by filtration and air dried.

PRODUCTION OF PYRROLE IV

Pyrrole IV is produced from 1,1 gram equivalents of boron trifluoride etherate and a 5 percent w/w solution in glacial acetic acid containing one gram equivalent of Pyrrole III; the Pyrrole III solution also contains 2 gram equivalents of sodium borohydride. The Pyrrole III solution is cooled with ice while the boron trifluoride etherate is added thereto dropwise, with stirring. After the addition is complete, the reaction mixture is allowed to warm to room temperature of about 22° and then to stand two hours at room temperature; stirring is continued throughout. Excess sodium borohydride is then destroyed by cautious additions of glacial acetic acid. The reaction mixture, a solution, is then poured into ice water; Pyrrole IV which precipitates is recovered by filtration and air dried.

PRODUCTION OF PYRROLE V

Pyrrole V is produced from a 5 percent w/w solution in dichloromethane containing 1 gram equivalent of Pyrrole IV and a 5 percent w/w solution in dichloromethane containing 4 gm equivalents of sulfuryl chloride. The Pyrrole IV solution is diluted with about 10 percent v/v diethyl ether and the sulfuryl chloride solution is added to the diluted Pyrrole IV solution. The reaction is conducted at room temperature with stirring, which is commenced before the sulfuryl chloride solution addition is started, and continued for about one hour after that addition is completed. Solvent is then removed from the reaction mixture, leaving a pale yellow oil. The oil is dissolved in a solution of water in acetone containing 20 percent v/v water and the solution is heated under reflux. The solution becomes acidic rapidly. After 20 minutes under reflux, enough sodium acetate to neutralize the acid and a small excess is added to the solution; heating is continued until the acetone is vaporized and an oil separates from the aqueous phase which remains. Upon cooling of the reaction mixture to room temperature, the oil forms a crystallized solid ("Pyrrole VII": Pyrrole V, except that D is CO$_2$H) which is suspended in a 5 percent w/w solution in glacial acetic acid and 4.8 percent w/w acetic anhydride containing 3 equivalents of anhydrous sodium acetate per equivalent of the Pyrrole VII. The resulting suspension is heated gently to 80° and stirred while a 5 percent w/w solution in glacial acetic acid containing 1 equivalent of iodine monochloride (based upon the Pyrrole VII) is added dropwise thereto. When the iodine monochloride addition is complete, the solution which has formed is cooled and mixed with an equal volume of water; hypophosphorous acid is added to remove excess iodine; and the solid which forms is recovered by filtration, washed with water, dried and suspended with 0.2 g platinum oxide in tetrahydrofuran. The resulting suspension is hydrogenated until the uptake of hydrogen ceases. The solution of Pyrrole V in tetrahydrofuran which results is separated from the platinum oxide by filtration; the tetrahydrofuran is replaced under reduced pressure with methanol; and the Pyrrole V is recovered by filtration.

PRODUCTION OF DIPYRROMETHANE I

Dipyrromethane I is produced from a 5 percent w/w solution in dichloromethane containing one g equivalent Pyrrole II, one g equivalent Pyrrole V and about 2 g Montmorillonite clay. The clay is added to the Pyrrole II solution, and the slurry which results is stirred for about 10 minutes. The clay is then separated by filtration and washed with dichloromethane; the wash is combined with the filtrate; evaporation of the dichloromethane leaves the Dipyrromethane I.

PRODUCTION OF PYRROLE VI

Pyrrole VI is produced from 6 g lead tetra-acetate and a solution of 1 g equivalent Pyrrole IV in 2 ml acetic anhydride and 100 ml glacial acetic acid. The lead tetra-acetate is added to the Pyrrole II solution, and the resulting reaction mixture is warmed on a steam bath to dissolve the lead tetra-acetate. The solution which is formed is stirred for 16 hours at room temperature of about 22°, after which time the Pyrrole VI is precipitated by dropwise addition of ice water, separated from the liquid by filtration, washed with water and air dried.

PRODUCTION OF DIPYRROMETHANE II

Dipyrromethane II is produced by dissolving Pyrrole VI in methanol containing about 0.05 percent w/w HCl to make a 5 percent w/w solution, and heating the solution under reflux for five hours. The reaction product is cooled to room temperature of about 22° and poured into ice water to precipitate the Dipyrromethane II, which is then recovered by filtration and air dried.

PRODUCTION OF DIPYRROMETHANE III

Dipyrromethane III is produced from 2 g Dipyrromethane II, 50 ml absolute ethanol containing 0.05 percent w/w triethyl amine, 0.1 g charcoal coated with 5 percent w/w palladium, 3 ml trifluoroacetic acid and 1.0 g p-nitrobenzoyl chloride dissolved in 1.0 g dry dimethyl formamide. The Dipyrromethane II is dissolved in the absolute ethanol and the palladium on charcoal is added to the resulting solution. The Dipyrromethane II is then hydrogenated in a sloping manifold hydrogenator in which a slight positive pressure of hydrogen is maintained until there is no longer an uptake of hydrogen. The palladium on charcoal is then separated from the reaction mixture by filtration, and the solvent is evaporated, leaving a solid white residue. The white residue is powdered finely and added, under nitrogen, to the trifluoroacetic acid at a temperature of 45°; the reaction mixture is maintained at 45°, with stirring, until the evolution of $CO_2$ subsides and for an additional 3 minutes, and is then poured into 30 ml 56 percent w/w aqueous ammonium hydroxide to which 5 g crushed ice has been added. The aqueous mixture which results is extracted with dichloromethane, which is then evaporated; the red oil which remains after evaporation of the dichloromethane is immediately dissolved in 3 ml dry dimethylformamide, and the solution which results is cooled to and maintained at 0°, with stirring, while the solution of p-nitrobenzoyl chloride in dimethyl formamide is added dropwise, and for 30 minutes after completion of the addition. An addition of 20 ml diethyl ether is made 15 minutes after completion of the addition of the dimethyl formamide solution, and, 15 minutes later, solids which have precipitated are separated from the liquid by filtration and added, with stirring, to 50 percent w/w aqueous ethanol containing about 3 g sodium carbonate, which has been heated to 70°. After 15 minutes of stirring, Dipyrromethane III is separated from the ethanol/water solution by filtration and air dried.

PRODUCTION OF PORPHYRIN I

Porphyrin I is produced from two solutions, one a 5 percent w/w solution in dry tetrahydrofuran containing 0.05 percent w/w triethyl amine and 1 g equivalent Dipyrromethane I, and the second a 5 percent w/w solution in dichloromethane containing 5 percent v/v methanol, 0.05 percent w/w p-toluenesulfonic acid and 1 g equivalent of Diprromethane III, using 5 percent w/w, based on the weight of the Dipyrromethane I, 5 percent w/w palladium on charcoal as a hydrogenation catalyst. The palladium on charcoal is added to the Dipyrromethane I solution and hydrogenation is carried out in a sloping manifold hydrogenator in which a slight positive pressure of hydrogen is maintained until the uptake of hydrogen stops. The palladium on charcoal is then separated from the reaction mixture by filtration and washed with dilute ammonium hydroxide. The filtrate is evaporated to dryness in vacuo, and the product which remains is dissolved in the ammonia washings; 12 percent w/w acetic acid is added to the resulting solution to adjust the pH to 4 and the temperature thereof is lowered to about 5° to cause precipitation of an intermediate diacid. The diacid is then dissolved in the second solution and the resulting reaction mixture is allowed to stand in the dark at room temperature of about 22° for 24 hours, after which time a methanolic solution containing about 1 g zinc acetate dihydrate is added thereto. The solution is allowed to stand in the dark at room temperature for another 72 hours, after which time the solvent is removed by evaporation, and the solid which remains is dissolved in aqueous dioxane containing 3 equivalents KOH per equivalent of Porphyrin I. The resulting solution is refluxed for four hours, cooled, and diluted with distilled water; the Porphyrin I is extracted from the solution with dichloromethane; the dichloromethane is evaporated; and the residue is recrystalled from a 50 percent v/v solution of methanol in dichloromethane.

PRODUCTION OF PORPHYRIN COMPLEX II

A 5 percent w/w solution in a mixed dichloromethanenethanol solvent containing 20 percent v/v methanol, 1 g equivalent of Porphyrin I and 2 g equivalents of nickel acetate is refluxed for 16 hours. The solvent is then evaporated until the Porphyrin Complex II precipitates; the product is recovered by filtration and air dried.

PRODUCTION OF PORPHYRIN COMPLEXES III-VI

A mixture of the porphyrin complexes identified above is prepared from 1 g Porphyrin Complex II, 28 ml freshly distilled phosphorus oxychloride, 20 ml dry dimethyl formamide and 750 ml dry 1,2-dichloroethane. The dimethyl formamide is cooled on an ice bath, and the phosphorus oxychloride is added thereto dropwise. The solution which results is allowed to stand at room temperature of about 22° for 30 minutes, and is then warmed to 50°. The Porphyrin Complex II is dissolved in the 1,2-dichloroethane, and the resulting solution is added dropwise, with stirring, to the phosphorus oxychloride; the addition is made over a period of about 30 minutes. The reaction mixture is maintained at about 50°, with stirring, for an additional 2 hours. The organic and the aqueous phases are then separated, and the aqueous phase is extracted with dichloromethane. The organic phase and the dichloromethane extract are then combined, and evaporated to dryness. The solid which remains is recrystallized from a solvent composed of equal parts by volume of dichloromethane and methanol, yielding a mixture of Porphyrin Complex III, Porphyrin Complex IV, Porphyrin Complex V and Porphyrin Complex VI. The mixture of complexes is separated by silica gel chromatography, using dichloromethane containing 1 percent v/v methanol as the eluant.

PRODUCTION OF PORPHYRIN COMPLEX VII

A solution of 506 mg Porphyrin Complex V and 1.024 g. (carbethoxymethylene)triphenylphosphorane in 50 ml xylene is heated under reflux for 18 hours. The solution is cooled; the xylene is removed in vacuo; and the solid which remains is dissolved in the minimum amount of dichloromethane and chromatographed on silica gel. A minor fraction of Porphyrin Complex V and a major red fraction are recovered. The solvent is removed from the red fraction; the solid which remains is recrystallized from a solvent composed of equal parts by volume of dichloromethane and methanol, yielding Porphyrin Complex VII.

PRODUCTION OF PORPHYRIN VIII

A solution of 621 mg Porphyrin Complex VII in 10 ml concentrated (96.7 percent w/w) sulfuric acid is prepared; after the solution stands for 2 hours at room temperature of about 22°, an addition of 100 ml dichloromethane is made thereto, followed by saturated aqueous sodium bicarbonate to neutralize the sulfuric acid. The organic layer is collected, washed and dried; the solvent is then vaporized. The crude product which remains is recrystallized from a solvent composed of equal parts by volume of dichloromethane and methanol, yielding Porphyrin VIII.

PRODUCTION OF PURPURIN II AND PURPURIN III

A solution of 100 mg Porphyrin VIII in 20 ml glacial acetic acid is heated under reflux in a nitrogen atmosphere for 24 hours. The solution is then cooled; the acetic acid is removed in vacuo; and the remaining product is dissolved in the minimum amount of dichloromethane and chromatographed on silica gel, yielding a major green fraction from which the solvent is removed. The remaining solid is recrystallized from 50 percent v/v dichloromethane and methanol, yielding a mixture of Purpurin II and Purpurin III which are separated by silica gel chromatography using dichloromethane and 1 percent v/v methanol as the elufant.

PRODUCTION OF PURPURIN V

Purpurin V is produced from 59 mg Purpurin II, 25 mg N,N'-carbonyldimidazole, 100 mg zinc acetate, 25 mg sodium hydride and 87 mg methyl t-butyl malonate. The Purpurin II is dissolved in 5 ml dichloromethane and refluxed for one hour with the N,N'-carbonyldiimidazole; the zinc acetate dissolved in 5 ml methanol is then added and the resulting reaction mixture is warmed gently for 5 minutes. After an addition of 25 ml dichloromethane, the solution which forms is washed three times with 50 ml portions of water, dried over $MgSO_4$ and evaporated under vacuum; the solid residue which remains after evaporation of the solvents is maintained at an absolute pressure of 0.1 mm Hg for 30 minutes, and is then dissolved in dichloromethane. The resulting solution is then added to a malonate anion solution prepared by adding the sodium hydride and the methyl t-butyl malonate to 10 ml tetrahydrofuran, and the reaction mixture is stirred for 40 minutes at room temperature of about 22° and added to 50 ml chloroform and 20 ml 1 normal hydrochloric acid. The organic phase is separated from the aqueous phase, washed twice with 50 ml portions of water, dried over $MgSO_4$ and evaporated; the residue is stirred at room temperature of about 22° with 5 ml trifluoroacetic acid for 40 minutes and the resulting product is mixed with 100 ml water and 50 ml chloroform. The organic layer is separated from the aqueous layer, washed twice with 50 ml portions of water dried over $MgSO_4$, and evaporated to dryness. The residue is dissolved in the minimum amount of dichloromethane containing 5 percent v/v acetone and purified by elutriation on alumina. Purpurin V is recovered by evaporating the solvents from the elutriate.

PRODUCTION OF PURPURIN IV

Purpurin IV is prepared from 68 mg Purpurin V and 110 mg thallium trifluoroacetate. A solution of the Purpurin V in 20 ml dry dichloromethane and 20 ml dry tetrahydrofuran is treated with a solution of the thallium trifluoroacetate in 10 ml dry tetrahydrofuran. After 2 minutes, the solution which results is placed in sunlight for about 10 minutes until a sample examined spectrophotometrically shows the expected shift of the Soret absorption band. The solution is then treated briefly with $SO_2$ gas, stirred for about 1 minute with about ½ ml 37 percent w/w hydrochloric acid, diluted with 50 ml dichloromethane, and washed three times with 100 ml portions of water. The solvents are then removed by evaporation; the residue is dissolved in dichloromethane containing 5 percent v/v methanol; the solution is chromatographed on alumina; and the Purpurin V is crystallized from the solvent and recovered by filtration.

PRODUCTION OF PURPURIN I

A solution of 60 mg sodium borohydride in 10 ml methanol is added dropwise to a solution of 200 mg Purpurin IV in 5 ml dichloromethane; the resulting solution is stirred at room temperature of about 22° for 2 hours, and is poured into 100 ml water. The organic phase is separated from the aqueous phase; the solvent is removed from the organic phase; and the solvent is evaporated. The residue is dissolved in 50 ml chloroform containing 25 percent v/v methanol; a 10 mg addition of p-toluene sulfonic acid is made; and the reaction mixture is refluxed for 6 hours. Water is then added to the reaction mixture; the organic layer is collected; and the solvent is removed by evaporation. The residue is dissolved in 5 ml dichloromethane containing 2 percent v/v methanol; the resulting solution is chromatographed on silica gel; and Purpurin I is recovered by evaporating the solvent from the chromatographed solution.

PRODUCTION OF DIMER I, DIMER II, DIMER III AND "DIMER IV

Dimers I through IV are produced from 1 g hematoporphyrin diacetate and a solution of 1 g Purpurin I in 50 ml solvent composed of 50 percent v/v 0.2 molar aqueous sodium hydroxide and tetrahydrofuran. The reaction mixture, initially the Purpurin I solution, is stirred vigorously: (1) in the dark for 16 hours, (2) while the hematoporphyrin diacetate is added gradually over a period of about 5 minutes, (3) for an additional 60 minutes and (4) thereafter, during the addition of a 5 ml portion of 1 molar aqueous sodium hydroxide. Additions of 0.1 molar HCl are then made to adjust the pH of the solution to 7.5. The organic phase is separated from the aqueous phase and purified by chromatography on a Sephadex column (LH-20); the solvent is removed under reduced pressure, and the mixture of Dimer I, Dimer II, Dimer III and Dimer IV which remains is stored in a freezer. The dimers are all composed of a Purpurin I moiety and a hematoporphyrin moiety in which is bivalent carbonyl group is bonded to the Purpurin moiety and to the oxygen of the hematoporphyrin moiety substituent that is a bivalent group having the structure $OCOCH_3$. The positions of these substituents are given in the following table:

| Compound | Bivalent Carbonyl of Purpurin I | Bivalent $OCHCH_3$ Group of hematoporphyrin |
|---|---|---|
| Dimer I | R9 | R2 |
| Dimer II | R9 | R4 |
| Dimer III | R15 | R2 |
| Dimer IV | R15 | R4 |

Hematoporphyrin diacetate is produced from 100 mg hematoporphyrin dichloride dissolved in 5 ml pyridine containing 10 percent v/v acetic anhydride. The solution is blanketed with $N_2$ for 4 hours, frozen on an acetone-solid $CO_2$ bath, and treated with 4 ml glacial acetic acid. The solid reaction product is then placed on an ice bath and allowed to warm with constant stirring. A total of 30 ml ice water is then added in increments, with stirring, to the solution of reaction products to precipitate the hematoporphyrin diacetate; the precipitated product is recovered by filtration and dried.

Figure 7:
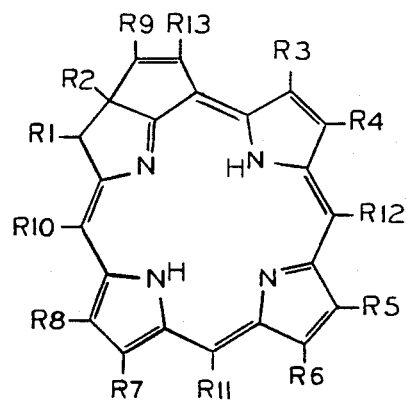
FIG. 7 is a structural formula for the family of purpurins having the structure of the complexes of FIG. 1; dimers according to the instant invention can be produced from these purpurins.
Figure 18:
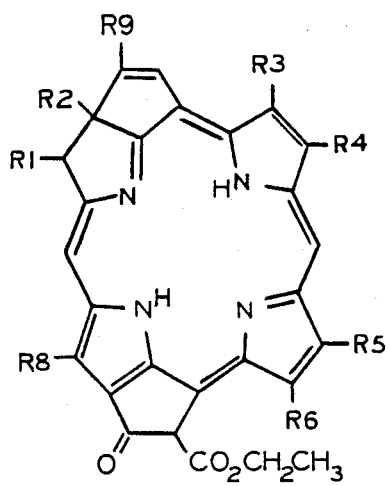
Figure 38:
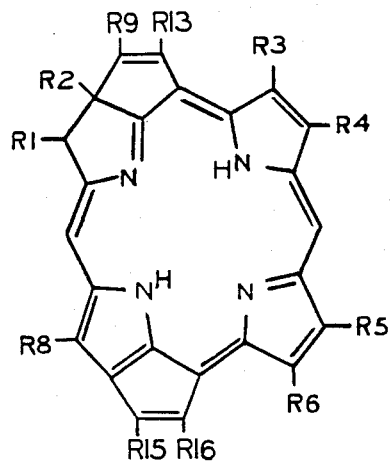

Purpurin II and Purpurin III are both produced from Porphyrin VIII in one step of the procedure described above as Example 1; Purpurin V, Purpurin IV and Purpurin I are then produced from Purpurin II. It will be appreciated that Purpurin III can be substituted for Purpurin II to produce the following isomers of Purpurin I, Purpurin IV and Purpurin V:

| Compound | Structure (referring to attached drawings) | |
|---|---|---|
| Purpurin VI | FIG. 38: | R1–R6 and R8 are $CH_2CH_3$<br>R9 is $CO_2CH_2CH_3$<br>R13 is H<br>R15 is $CO_2CH_2CH_3$ |
| Purpurin VII | FIG. 18: | R1–R6 and R8 are $CH_2CH_3$<br>R9 is $CO_2CH_2CH_3$ |
| Purpurin VIII | FIG. 7: | R1–R6 and R8 are $CH_2CH_3$<br>R7 is $(O=C)CH_2CO_2CH_3$<br>R9 is $CO_2CH_2CH_3$<br>R10–R13 are hydrogen |

Figure 10:
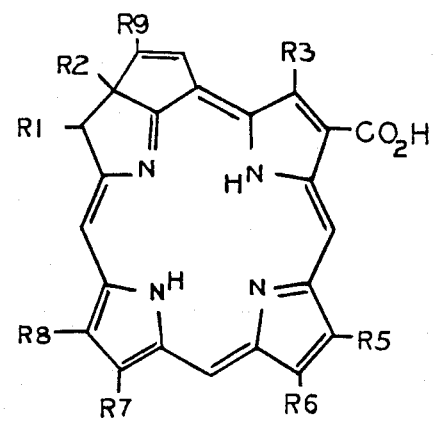
Figure 15:
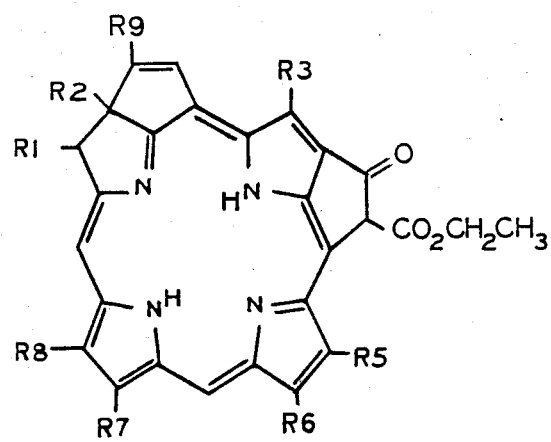
Figure 35:
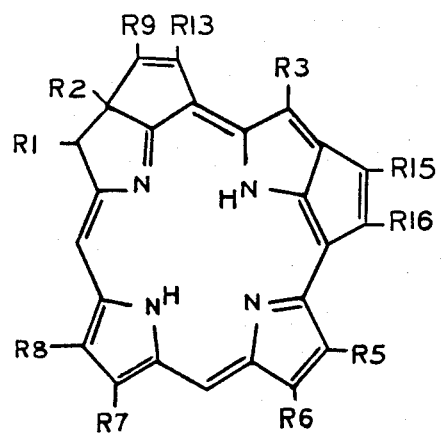

Similarly, Porphyrin Complex III, Porphyrin Complex IV, Porphyrin Complex V and Porphyrin Complex VI are all produced in one step of the procedure; Porphyrin Complex VII, Porphyrin VIII, Purpurin II and Purpurin III are then produced from Porphyrin Complex V. It will be appreciated that Porphyrin Complex IV can be substituted for Porphyrin Complex V to produce the following isomers of Porphyrin Complex VII, Porphyrin VIII, Purpurin I, Purpurin II, Purpurin IV and Purpurin V:

| Compound | Structure (referring to attached drawings) | |
|---|---|---|
| Porphyrin Complex IX | FIG. 6: | R, R11 and R12 are hydrogen<br>R1 and R3–R8 are $CH_2CH_3$<br>R2 is $CO_2H$<br>R10 is $CH=CHCO_2CH_2CH_3$<br>M is Ni |
| Porhyrin X | FIG. 3: | R, R11 and R12 are hydrogen<br>R1 and R3–R8 are $CH_2CH_3$<br>R2 is $CO_2H$<br>R10 is $CH=CHCO_2CH_2CH_3$ |
| Purpurin IX | FIG. 35: | R1–R3 and R5–R8 are $CH_2CH_3$<br>R9 is $CO_2CH_2CH_3$<br>R13 is H<br>R15 is $CO_2CH_2CH_3$ |
| Purpurin X | FIG. 10: | R1–R3 and R5–R8 are $CH_2CH_3$<br>R9 is $CO_2CH_2CH_3$ |
| Purpurin XI | FIG. 15: | R1–R3 and R5–R8 are $CH_2CH_3$<br>R9 is $CO_2CH_2CH_3$ |
| Purpurin XII | FIG. 7: | R1–R3 and R5–R8 are $CH_2CH_3$<br>R4 is $(O=C)CH_2CO_2CH_3$<br>R9 is $CO_2CH_2CH_3$<br>R10–R13 are hydrogen |

Figure 11:
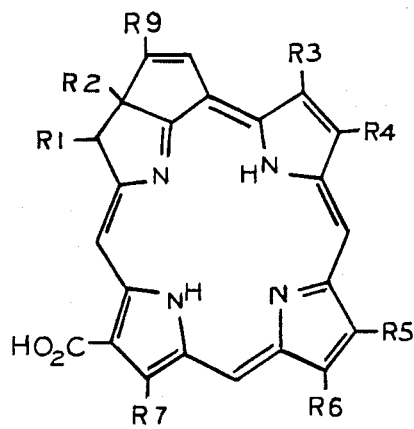
Figure 12:
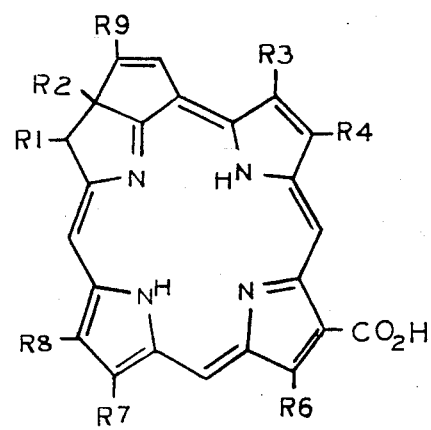

Similarly, it will be appreciated that Porphyrin Complex VI can be substituted for Porphyrin Complex V to produce the following isomers of Porphyrin Complex VII, Porphyrin VIII and Purpurin II:

| Compound | Structure (referring to attached drawings) | |
|---|---|---|
| Porphyrin Complex XI | FIG. 6: | R, R10 and R11 are hydrogen<br>R1 and R3–R8 are $CH_2CH_3$<br>R2 is $CO_2H$<br>R12 is $CH=CHCO_2CH_2CH_3$<br>M is Ni |
| Porphyrin XII | FIG. 3: | R, R10 and R11 are hydrogen<br>R1 and R3–R8 are $CH_2CH_3$<br>R2 is $CO_2H$<br>R12 is $CH=CHCO_2CH_2CH_3$ |
| Purpurin XIII | FIG. 11: | R1–R7 are $CH_2CH_3$<br>R9 is $CO_2CH_2CH_3$ |
| Purpurin XIV | FIG. 12: | R1–R4 and R6–R8 are $CH_2CH_3$<br>R9 is $CO_2CH_2CH_3$ |

Figure 16:
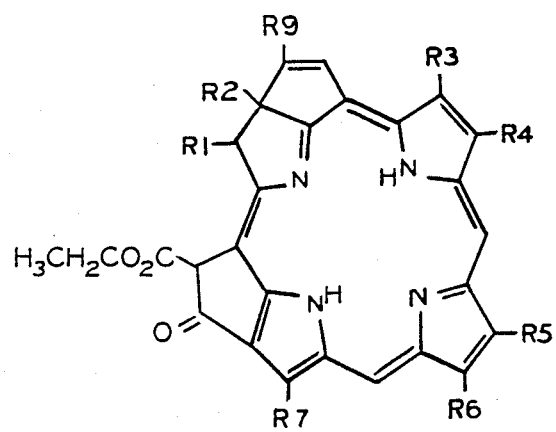
Figure 17:
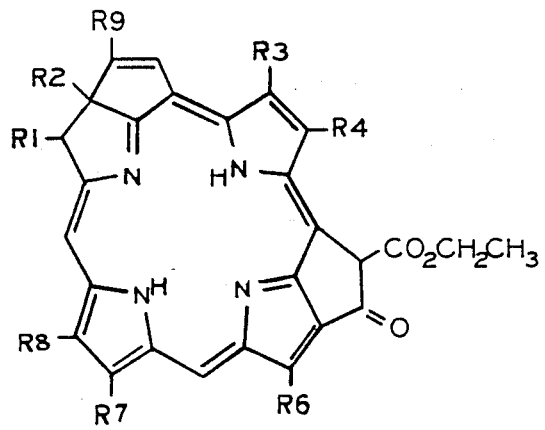
Figure 36:
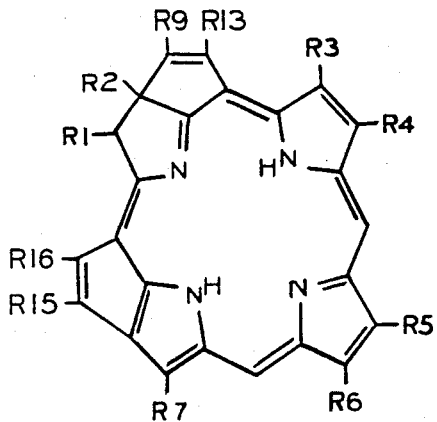
Figure 37:
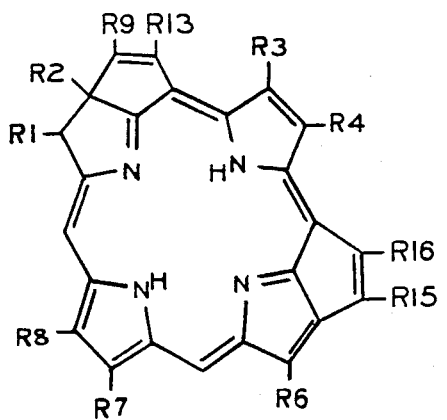
Figure 39:
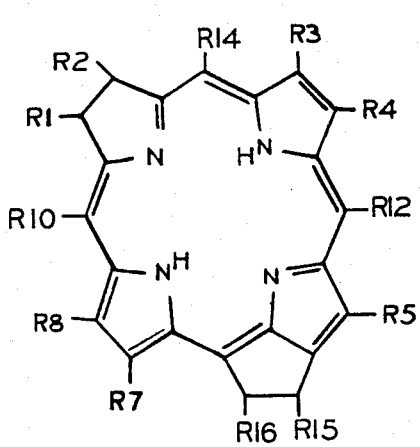
FIGS. 39-43 are structural formulas for chlorins which can be produced from purpurins having the formulas of FIGS. 29-33, and from which dimers according to the invention can be produced.
Figure 40:
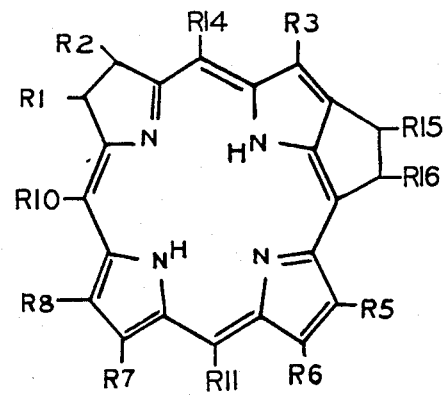
Figure 43:
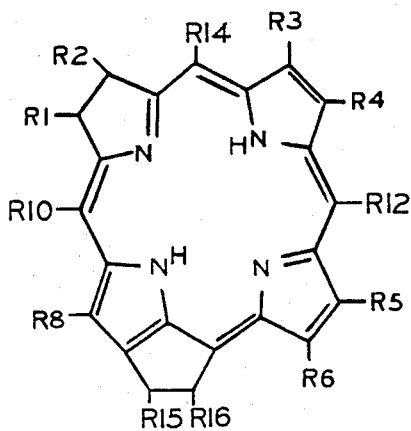
Figure 41:
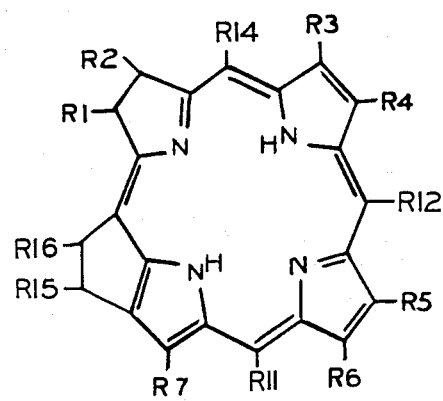
Figure 42:
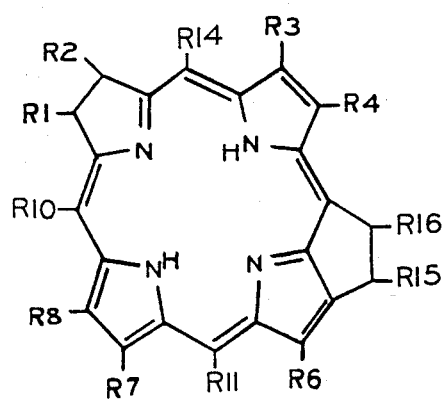
Figure 44:
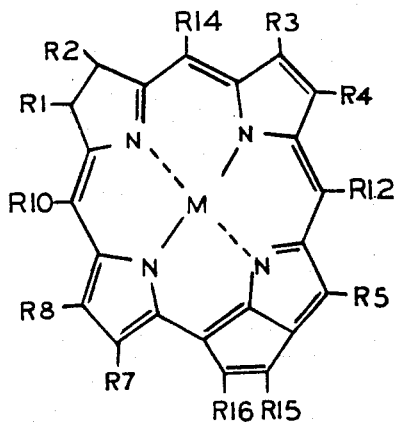
FIGS. 44-48 are structural formulas for metal complexes of purpurins having the formulas of FIGS. 29-33 dimers according to the instant invention can be produced from these complexes.
Figure 45:
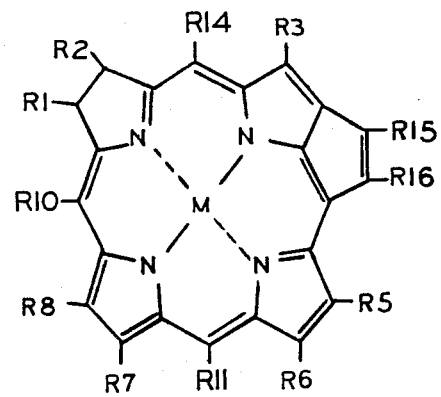
Figure 48:
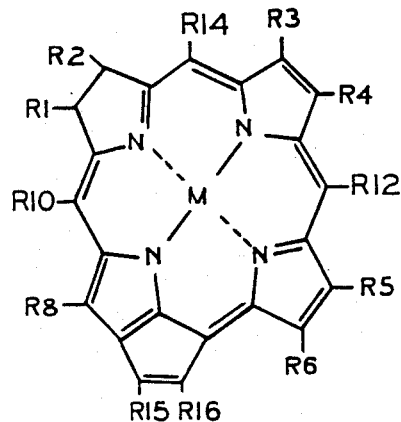
Figure 46:
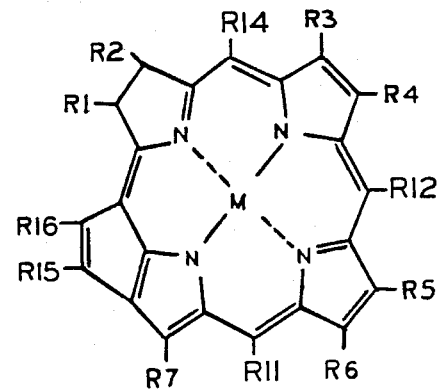
Figure 47:
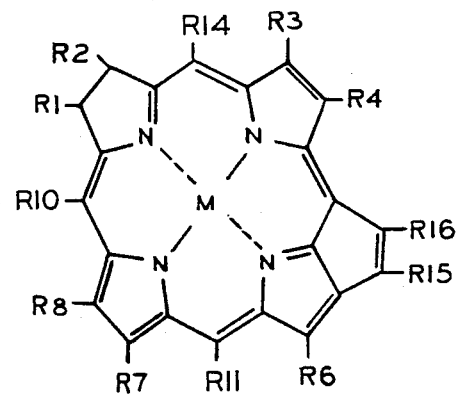
Figure 49:
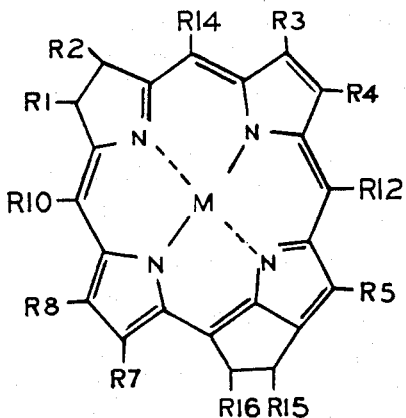
Figure 50:
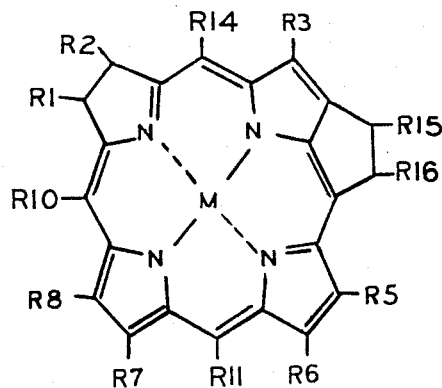
Figure 53:
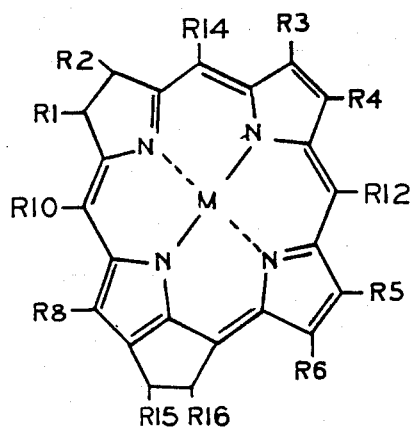
Figure 51:
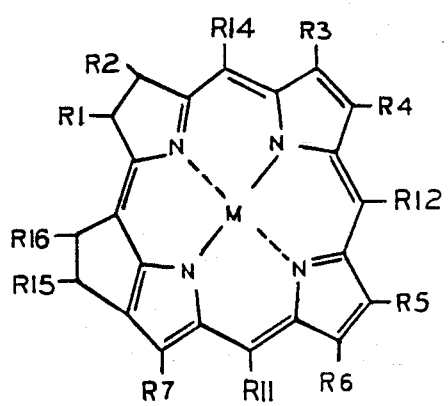
Figure 52:
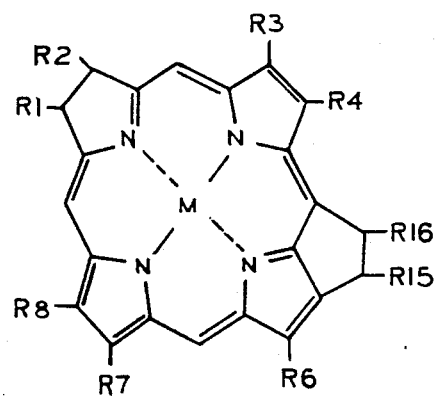
Figure 54:
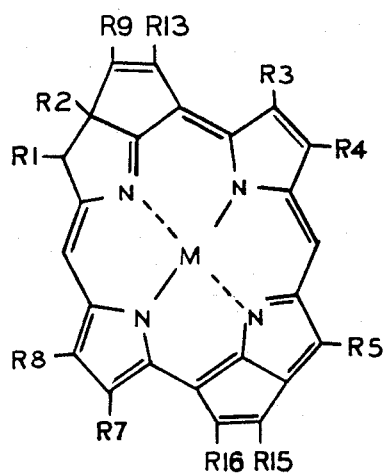
Figure 55:
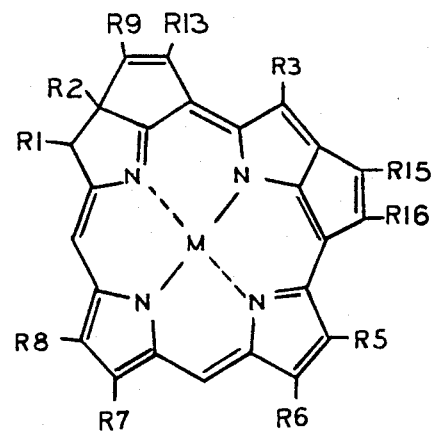
Figure 58:
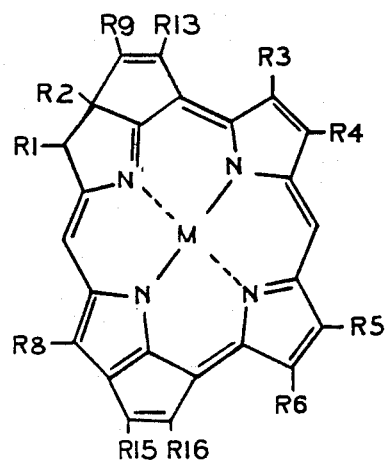
Figure 56:
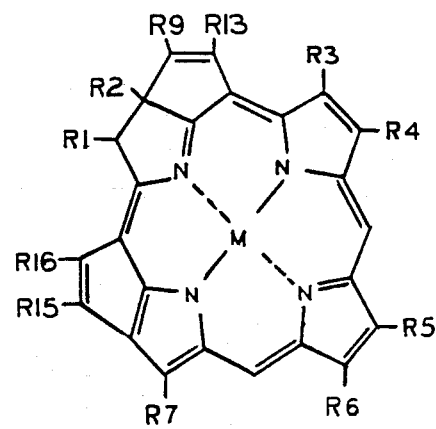
Figure 57:
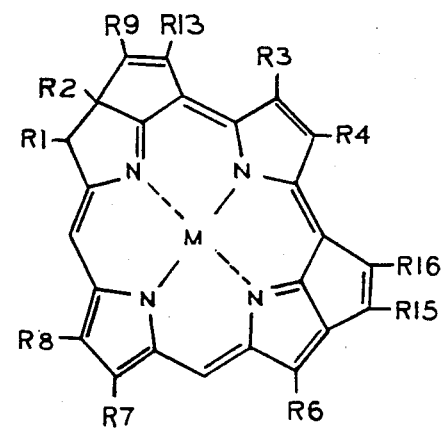

In a like manner, Purpurins XIII and XIV can be substituted for Purpurin II to produce other isomers of Purpurin I:

| Compound | Structure (referring to attached drawings) | |
|---|---|---|
| Purpurin XV | FIG. 36: | R1–R7 are $CH_2CH_3$<br>R9 is $CO_2CH_2CH_3$<br>R13 is H<br>R15 is $CO_2CH_2CH_3$ |
| Purpurin XVI | FIG. 16: | R1–R7 are $CH_2CH_3$<br>R9 is $CO_2CH_2CH_3$ |
| Purpurin XVII | FIG. 7: | R1–R7 are $CH_2CH_3$<br>R8 is $(O=C)CH_2CO_2CH_3$<br>R9 is $CO_2CH_2CH_3$<br>R10–R13 are hydrogen |
| Purpurin XVIII | FIG. 37: | R1–R4 and R6–R8 are $CH_2CH_3$<br>R9 is $CO_2CH_2CH_3$<br>R13 is H<br>R15 is $CO_2CH_2CH_3$ |
| Purpurin XIX | FIG. 17: | R1–R4 and R6–R8 are $CH_2CH_3$<br>R9 is $CO_2CH_2CH_3$ |
| Purpurin XX | FIG. 7: | R1–R4 and R6–R8 are $CH_2CH_3$<br>R5 is $(O=C)CH_2CO_2CH_3$ |

-continued

| Compound | Structure (referring to attached drawings) |
|---|---|
| | R9 is $CO_2CH_2CH_3$ |
| | R10–R13 are hydrogen |

Other dimers according to the invention can be produced by substituting equivalent amounts of any of purpurins II through XX for Purpurin I in the procedure of Example 1. Two isomers are produced in all cases, one where R2 and the other where R4 of the hematoporphyrin moiety is the bivalent group having the structure $OCHCH_3$ where the carbon bonded to oxygen is also bonded to the hematoporphyrin and the oxygen is bonded to a bivalent carbonyl group of the purpurin. In all of the dimers, the bivalent carbonyl group can be R9 of the purpurin; in addition: in Purpurins V, VI, VIII and IX it can be R6, R7, R15 or R16; in Purpurins XII, XV and XVII it can be R4, R8 or R15; and in Purpurins XVIII and XX it can be R5 or R15.

Similarly, a purpurin alcohol can be made from any of purpurins I through XX, and the purpurin alcohol can be reacted by the procedure of Example 1 with any of purpurins I through XX to produce a dimer composed of two purpurin moieties bonded to one another through a carbonyl group. The following example illustrates reactions of these types.

EXAMPLE 2

A purpurin alcohol (hereafter Purpurin Alcohol II) is produced from a stirred solution of 100 mg Purpurin II dissolved in 25 ml tetrahydrofuran and 50 mg $LiAlH_4$. The $LiAlH_4$ is added to the Purpurin II solution, and the suspension which results is stirred for two hours at room temperature of about 22°. The reaction mixture is then poured into 200 ml water; 2 molar HCl is added to make the solution slightly acidic; and Purpurin Alcohol II is extracted from the slightly acidic solution with dichloromethane. The organic phase is separated from the aqueous phase, and the solvent is evaporated from the former. Purified Purpurin Alcohol II is then recovered from the solid residue by recrystallization in the minimum amount of dichloromethane containing 10 percent v/v methanol.

A dimer according to the invention is produced from 1 g Purpurin Alcohol II and a solution of 1 g Purpurin II in 50 ml solvent composed of 50 percent v/v 0.2 molar aqueous sodium hydroxide and tetrahydrofuran. The reaction mixture, initially the Purpurin II solution, is stirred vigorously: (1) in the dark for 16 hours, (2) while the Purpurin Alcohol II solution is added gradually over a period of about 5 minutes, (3) for an additional 60 minutes and (4) thereafter, during the addition of a 5 ml portion of 1 molar aqueous sodium hydroxide. Additions of 0.1 molar HCl are then made to adjust the solution to a pH of 7.5. The organic phase is separated from the aqueous phase and purified by chromatography on a Sephadex column (LH-20); the solvent is removed under reduced pressure, and the dimer which remains is stored in a freezer. The dimer is composed of two Purpurin II moieties which are bonded to one another through a carbonyl group.

Other dimers according to the invention can be produced by making amines of any of purpurins I through XX and reacting those amines with hematoporphyrin to produce purpurin/hematoporphyrin amides. The production of an amide dimer of hematoporphyrin and Purpurin II is described in the following example.

EXAMPLE 3

Ammonia gas is bubbled for 2 hours through a solution of 20 mg Purpurin II in 50 ml tetrahydrofuran. The solvent is then evaporated from the reaction mixture; the solid which precipitates is redissolved in 50 ml tetrahydrofuran; and a 10 mg portion of $LiAlH_4$ is added to the solution. The reaction mixture which results is stirred for 2 hours at room temperature of about 22°, and is then poured into 200 ml water; 2 molar HCl is added to make the solution slightly acidic; and the organic phase is extracted from the slightly acidic solution with dichloromethane. The organic phase is separated from the aqueous phase, and the dichloromethane is evaporated from the former. A purified amine (hereafter Purpurin Amine II) is then recovered from the solid residue by recrystallization from the minimum amount of dichloromethane containing 10 percent v/v methanol. The amine has the FIG. 9 structure where R1–R5, R7 and R8 are $CH_2CH_3$ and R9 is $CH_2NH_2$.

A mixture of dimers according to the instant invention is then produced from a solution of 20 mg hematoporphyrin in 1.25 ml water and 0.8 ml N,N-dimethyl formamide, a solution of 20 mg 1-ethyl-3-(3-dimethylaminopropyl)-carbodiimide.HCl in 0.6 ml water, and a solution of 15 mg Purpurin Amine II dissolved in a mixed solvent composed of 5 ml water and 1 ml N,N-dimethyl formamide. The hemato porphyrin solution and the carbodiimide solution are mixed with one another, and the resulting solution is mixed with the amine solution. A mixture of dimers according to the invention is recovered by chromatographing the reaction mixture on a Sephadex column and removing the solvent under reduced pressure. The dimers are composed of a hematoporphyrin moiety and a Purpurin Amine II moiety chemically bonded to one another through a bivalent carbonyl group which is a part of one of the R substituents of the hematoporphyrin moiety and is bonded to a nitrogen of the R9 substituent ($NHCH_2$) of the Purpurin Amine II moiety. Specifically, the bivalent carbonyl group is a part of either the R6 or the R7 substituent of the hematoporphyrin moiety, and the substituent has the structure $CH_2CH_2CO$.

The procedure of the second paragraph of Example 3 can also be used to produce dimers of two purpurins. This procedure is exemplified in the following example.

EXAMPLE 4

A dimer according to the instant invention is produced from a solution of 20 mg Purpurin II in 1.25 ml water and 0.8 ml N,N-dimethyl formamide, a solution of 20 mg 1-ethyl-3-(3-dimethylaminopropyl)-carbodiimide.HCl in 0.6 ml water, and a solution of 15 mg Purpurin Amine II dissolved in a mixed solvent composed of 5 ml water and 1 ml N,N-dimethyl formamide. The Purpurin II solution and the carbodiimide solution are mixed with one another, and the resulting solution is mixed with the amine solution. A dimer according to the invention (hereafter Dimer V) is recovered by chromatographing the reaction mixture on a Sephadex column and removing the solvent under reduced pressure. Dimer V is composed of Purpurin II and Purpurin Amine II moietiis chemically bonded through a bivalent carbonyl group which has replaced the $CO_2H$ substituent of the Purpurin II moiety and is bonded to a nitrogen of the R9 substituent ($NHCH_2$) of the Purpurin II Amine moiety.

Other dimers comprising two moieties chemically linked to one another through a CONH group can be produced from amines made by the procedure of the first paragraph of Example 3 from Purpurin I or from one of Purpurins III through XX. The amines can be reacted to produce dimers with hematoporphyrin by the method of the second paragraph of Example 3. Any of these amines or Purpurin Amine II can also be reacted by the method of Example 4 to produce dimers with any of Purpurins I through XX. Reaction is possible, also, by the method of Example 4, between any purpurin amine and the carboxyl group of Purpurin II, Purpurin III, Purpurin X, Purpurin XIII and Purpurin XIV.

It will be appreciated that other purpurins having the structures of FIGS. 7, 9–18, 29–33 and 34–38 can be produced by the method of Example 1 from porphyrins having an appropriate structure, if available, or synthesized from dipyrromethanes having an appropriate structure, if available; further, the requisite dipyrromethanes can be synthesized by the method set forth from available pyrroles or from pyrroles synthesized as described. Purpurins so produced have the structure of one of the indicated figures of the drawings where each of R1 through R8 is H, a primary or secondary alkyl group having from 1 to 4 carbon atoms, an alkylene group having from 2 to 4 carbon atoms, a group having the formula $R_2N(R_3)_2$ where $R_2$ is a bivalent aliphatic hydrocarbon radical having from 1 to 4 carbon atoms, wherein any carbon to carbon bond is either a single or a double bond, and not more than one is a double bond; $R_3$ is hydrogen or an alkyl group having from 1 to 2 carbon atoms and the two $R_3$ groups can be the same or different, a group having the formula $R_2N(R_4)_3^+$ where $R_2$ is a bivalent aliphatic hydrocarbon radical having from 1 to 4 carbon atoms, wherein any carbon to carbon bond is either a single or a double bond, and not more then one is a double bond; and $R_4$ is an alkyl group having from 1 to 2 carbon atoms and the three $R_4$ groups can be the same or different, a group having the formula $R_2OH$ were $R_2$ is a bivalent aliphatic hydrocarbon radical having from 1 to 4 carbon atoms, wherein any carbon to carbon bond is either a single or a double bond, and not more than one is a double bond, or $CO_2R'$, $CH_2CO_2R'$ or $CH_2CH_2CO_2R'$ where R' is H, or a primary or secondary alkyl group having from one to four carbon atoms.

In the purpurins so produced, R9 and R15 are usually $CO_2CH_3$ or $CO_2CH_2CH_3$, their identity being determined by that of the precursor porphyrin (see steps of producing Porphyrin Complex VII, Porphyrin VIII, and Purpurins II and III in Example 1; the identity of the $CO_2CH_2CH_3$ groups in Purpurins II and III was determined by that of the β-ethoxycarbonylvinyl moiety in Porphyrin VIII), and R10 through R14 are hydrogen. Dimers according to the instant invention can be made from any of the above purpurins where one of R1 through R16 is $CO_2R'$, $CH_2CO_2R'$ or $CH_2CH_2CO_2R'$ by substituting them for Purpurin II in the Example 1 procedure. In addition, an amine can be produced by the method of the first paragraph of Example 3 from any of the foregoing purpurins where one of R1 through R16 is one for the indicated groups, and the amine can be substituted for Purpurin Amine II in the procedure of the second paragraph of Example 3 or in the procedure of Example 4, or a purpurin alcohol can be produced by the method of Example 2 from any of the foregoing purpurins where one of R1 through R16 is $CO_2R'$, $CH_2CO_2R'$ or $CH_2CH_2CO_2R'$, and a dimer according to the invention can be produced by the method of Example 2 from that alcohol and any of the foregoing purpurins where one of R1 through R16 is $CO_2R'$ or the like. In Purpurins II, III, X, XIII and XIV, reaction is also possible between the carboxy substituent and the purpurin alcohol.

Where any of R1 through R16 of any of the foregoing purpurins is $CO_2H$, that purpurin can be reacted with an amino acid moiety, which can be a monoclonal antibody, to form an amide. Example 5 is illustrative of such reactions:

EXAMPLE 5

A dimer according to the invention coupled to a monoclonal antibody is produced from 40 mg dimer produced as described in Example 2 dissolved in 2.5 ml water and 1.6 ml N,N-dimethyl formamide, 20 mg 1-ethyl-3-(3-dimethylaminopropyl) carbodiimide.HCl dissolved in 0.6 ml water and 15 mg monoclonal antibody dissolved in 5 ml distilled water. The dimer solution is added to the carbodiimide hydrochloride solution, and the combined solution is mixed with the monoclonal antibody solution. After 30 minutes, the reaction is quenched by adding 0.05 ml monoethanol amine, and the conjugated material, i.e., the amide of the monoclonal antibody and the dimer starting material (hereafter Dimer VI), is dialyzed exhaustively at 4° against 0.001N phosphate buffered saline, pH 7.4.

The procedure of Example 5 can be used to couple other proteins, other amino acids, to other dimers according to the invention, provided that the other dimers have a $CO_2H$ group. Similarly, the procedure of Example 5 can be modified by substitution for the dimer starting material of an equivalent amount of hematoporphyrin or of a purpurin, of a chlorin or of a complex having a $CO_2H$ group in its structure to produce an amide of hematoporphyrin, of a purpurin, of a chlorin or of a complex. A dimer can then be produced from the amide, for example by the procedure of any of Examples 1 through 4 hereof.

It is known that some monoclonal antibodies, after they have been administered to a patient, for example intravenously, localize in tumor cells, specifically in malignant tumor cells. It is also known that some purpurins and some chlorins, after administration, localize in a similar manner and can then be detected with ultra violet light, which causes them to fluoresce, or illuminated with visible light of a wavelength at which they show an absorbance peak, which causes them to undergo a reaction which destroys the tumor in which they have localized; as is disclosed in pending application Ser. No. 842,125, filed Mar. 18, 1986, this has been shown to be true of several purpurins having the formula of FIG. 7 of the attached drawings and for several chlorins having the formula of FIG. 8. It will be appreciated, therefore, that a purpurin or chlorin with a monoclonal antibody which localizes in this way chemically attached thereto has an enhanced capability to localize and the same capability for detection and destruction of a tumor where it has localized, by comparison with the parent purpurin or chlorin. The purpurin produced as described in Example 1 is such as purpurin; the corresponding chlorin can be produced therefrom by the procedure of Example 8 infra. It will be also be appreciated that dimers according to the instant invention will also localize in tumor cells and can then be detected with ultra violet light or illuminated with visible light of a wavelength at which they show an absorbance peak to cause a reaction which destroys the tumor.

Some of the following data, Examples 6 through 12, is also disclosed in application Ser. No. 842,125, now abandoned, and in application Ser. No. 874,097, filed June 12, 1986.

EXAMPLE 6

The production of a purpurin (hereafter "Purpurin NT2") from nickel meso-formyl octaethyl porphyrin is described in this Example. The production of nickel meso-formyl octaethyl porphyrin is described in a journal article by R. Grigg et al., J. Chem. Soc. Perkin Trans I, 1972, pp. 1789, 1798; it has the formula of FIG. 6 of the attached drawings where R1 through R8 are ethyl, R is CHO, R10 through R12 are hydrogen, and M is Ni. Two intermediates were produced in the Example 6 procedure, nickel meso-($\beta$-ethoxycarbonylvinyl)octaethyl porphyrin, which has the formula of FIG. 6 of the attached drawings where R1 through R8 are ethyl, R is CH=CHCO$_2$CH$_2$CH$_3$, R10 through R12 are hydrogen, and M is Ni, and meso($\beta$-ethoxycarbonylvinyl)octaethyl porphyrin, which has the formula of FIG. 3 of the attached drawings where R1 through R8 are ethyl, R is CH=CHCO$_2$CH$_2$CH$_3$, and R10 through R12 are hydrogen. Purpurin NT2 has the formula of FIG. 7 of the attached drawings where R1 through R8 are ethyl, R9 is CO$_2$CH$_2$CH$_3$, and R10 through R13 are hydrogen.

Production of nickel meso-($\beta$-ethoxycarbonylvinyl)octaethyl porphyrin

A solution of 506 mg nickel meso-formyl octaethyl porphyrin and 1,024 g (carbethoxymethylene)triphenylphosphorane in 50 ml xylene was heated under reflux for 18 hours. The solution was cooled; the xylene was removed in vacuo; and the solid which remained was dissolved in the minimum amount of dichloromethane and chromatographed on silica. A minor fraction of nickel octaethyl porphyrin and a major red fraction were recovered. The solvent was removed from the red fraction; the solid which remained was recrystallized from a solvent composed of equal parts by volume of dichloromethane and methanol, yielding 455 mg small brown needles. The product was identified by nuclear magnetic resonance as nickel meso-($\beta$-ethoxycarbonylvinyl)-octaethyl porphyrin; it showed visible spectrum absorbance peaks at 405, 530 and 565 nanometers ($\epsilon$ 94 180, 18 604, 27 790).

Production of Meso-($\beta$-ethoxycarbonylvinyl)octaethyl porphyrin

A solution was prepared by dissolving 621 mg nickel meso-($\beta$-ethoxycarbonylvinyl)octaethyl porphyrin in 10 ml concentrated (96.7 percent w/w sulfuric acid; after the solution stood for 2 hours at room temperature of about 22°, an addition of 100 ml dichloromethane was made thereto, followed by saturated aqueous sodium bicarbonate to neutralize the sulfuric acid. The organic layer was collected, washed and dried; the solvent was then vaporized. The crude product which remained was recrystallized from a solvent composed of equal parts by volume of dichloromethane and methanol, yielding 552 mg small reddish-brown crystals which were identified by nuclear magnetic resonance as meso-($\beta$-ethoxycarbonylvinyl)octaethyl porphyrin. The production of this porphyrin is disclosed in a Journal article by Fuhrhop et al., Ann. Chem., 1976, pp. 1539-1559.

Production of Purpurin NT2

A solution of 100 mg meso-($\beta$-ethoxycarbonylvinyl)octaethyl porphyrin in 20 ml glacial acetic acid was heated under reflux in a nitrogen atmosphere for 24 hours. The solution was then cooled; the acetic acid was removed in vacuo; and the remaining product was dissolved in the minimum amount of dichloromethane and chromatographed on silica, yielding a major green fraction from which the solvent was removed. The solid which remained was recrystallized from 50 percent v/v dichloromethane and methanol yielding 68 mg purple microcrystals which were identified by nuclear magnetic resonance as Purpurin NT2, and found to have visible spectrum absorbance peaks at 433, 453, 503, 530, 568, 648 and 695 nanometers ($\epsilon$ 89 509, 89 509, 14 571, 12 143, 18 908, 10 582, 42 673).

Dimer VII is produced by the method of Example 1 from 1 g hematoporphyrin diacetate and a solution of 1 g Purpurin NT2 in 50 ml solvent composed of 50 percent v/v 0.2 molar aqueous sodium hydroxide and tetrahydrofuran.

An amine is produced from Purpurin NT2 (Purpurin Amine NT2) by the method of the first paragraph of Example 3. Dimer VIII is then produced by the method of the second paragraph of Example 3 from a solution of 20 mg hematoporphyrin in 1.25 ml water and 0.8 ml N,N-dimethyl formamide, a solution of 20 mg 1-ethyl-3(3-dimethylaminopropyl)-carbodiimide.HCl in 0.6 ml water, and a solution of 15 mg Purpurin Amine NT2 in a mixed solvent composed of 5 ml water and 1 ml N,N-dimethyl formamide.

Dimer IX is produced by the method of Example 4 from a solution of 20 mg Purpurin II in 1.25 ml water and 0.8 ml N,N-dimethyl formamide, a solution of 20 mg 1-ethyl-3-(3-dimethylaminopropyl)-carbodiimide.HCl in 0.6 ml water, and a solution of 15 mg Purpurin Amine NT2 in a mixed solvent composed of 5 ml water and 1 ml N,N-dimethyl formamide.

EXAMPLE 7

Production of Zn Purpurin NT2

A solution was prepared by dissolving 20 mg Purpurin NT2 in a mixed solvent composed of 15 ml dichloromethane and 5 ml methanol and 100 mg zinc acetate was added to the solution; the mixture which resulted was refluxed for about 4 minutes until the electronic spectrum of the reaction mixture indicated that chelation was complete. The reaction mixture was then concentrated to 7 ml and allowed to cool to room temperature of about 22°. Product which precipitated was recovered by filtration, dissolved in a mixed solvent composed of 5 ml dichloromethane and 2 ml methanol, and recrystallized, yielding 18 mg Zn Purpurin NT2 in the form of microcrystals. The Zn Purpurin NT2, a metal complex, has the formula of FIG. 1 of the attached drawings where R1 through R8 are ethyl, R9 is CO$_2$CH$_2$CH$_3$, R10 through R13 are hydrogen and M is Zn; the compound has visible spectrum absorbance peaks at 413, 435, 535, 578, 618 and 663 nanometers ($\epsilon$ 195 270, 219 498, 14 052, 18 886, 28 588, 86 733).

Dimer X is produced by the method of Example 1 from 1 g hematoporphyrin diacetate and a solution of 1 g Zn Purpurin NT2 in 50 ml solvent composed of 50 percent v/v 0.2 molar aqueous sodium hydroxide and tetrahydrofuran.

An amine is produced from Zn Purpurin NT2 (Zn Purpurin Amine NH2) by the method of the first paragraph of Example 3. Dimer XI is then produced by the method of the second paragraph of Example 3 from a solution of 20 mg hematoporphyrin in 1.25 ml water and 0.8 ml N,N-dimethyl formamide, a solution of 20 mg 1-ethyl-3(3-dimethylaminopropyl)-carbodiimide.HCl in 0.6 ml water, and a solution of 15 mg Zn Purpurin Amine NT2 in a mixed solvent composed of 5 ml water and 1 ml N,N-dimethyl formamide.

Dimer XII is produced by the method of Example 4 from a solution of 20 mg Purpurin II in 1.25 ml water and 0.8 ml N,N-dimethyl formamide, a solution of 20 mg 1-ethyl-3-(3-dimethylaminopropyl)-carbodiimide.HCl in 0.6 ml water, and a solution of 15 mg Zn Purpurin Amine NT2 in a mixed solvent composed of 5 ml water and 1 ml N,N-dimethyl formamide.

EXAMPLE 8

Production of "Chlorin NT2H2"

A solution was prepared by dissolving 100 mg Purpurin NT2 in 20 mg tetrahydrofuran and adding 2 drops of triethylamine; with stirring, an addition of 20 mg palladium on charcoal was made and the mixture which resulted was hydrogenated at room temperature of about 22° for 5 hours in a sloping manifold hydrogenator in which a slight positive pressure of hydrogen was maintained. The palladium on charcoal that was used was composed of 10 percent w/w of palladium and 90 percent w/w of charcoal. The palladium on charcoal was filtered from the colorless reaction mixture, and the filtrate was stirred vigorously while exposed to air until the solution turned brown, about 2½ hours. The solvent was then removed in vacuo, and the residue was dissolved in the minimum dichloromethane containing 1 percent v/v of methanol and chromatographed on silica. A major blue band was collected; the solvent was removed; and th crude product was dissolved in 5 ml dichloromethane containing 1 percent v/v of methanol and recrystallized, yielding 72 mg brown microprisms which were identified by nuclear magnetic resonance as Chlorin NT2H2, a compound having the formula of FIG. 8 of the drawings where R1 through R8 are ethyl, R9 is $CO_2CH_2CH_3$, and R10 through R13 are hydrogen. Chlorin $NT_2H_2$ was found to have absorbance peaks in the visible spectrum at 403, 500, 535, 558, 610 and 660 nanometers ($\epsilon$ 114 650, 23 532, 5 662, 4 246, 8 493, 39 455). The Chlorin $NT_2H_2$ zinc complex was prepared by the method described in Example 7; it was found to have absorbance peaks in the visible spectrum at 408, 515, 545, 590 and 633 nanometers ($\epsilon$ 145 474, 9 858, 5 377, 15 832, 59 444).

Dimer XIII is produced by the method of Example 1 from 1 g hematoporphyrin diacetate and a solution of 1 g Chlorin NT2H2 in 50 ml solvent composed of 50 percent v/v 0.2 molar aqueous sodium hydroxide and tetrahydrofuran.

An amine (Chlorin Amine NT2H2) is produced from Chlorin NT2H2 by the method of the first paragraph of Example 3. Dimer XIV is then produced by the method of the second paragraph of Example 3 from a solution of 20 mg hematoporphyrin in 1.25 ml water and 0.8 ml N,N-dimethyl formamide, a solution of 20 mg 1-ethyl-3(3-dimethylaminopropyl)-carbodiimide.HCl in 0.6 ml water, and a solution of 15 mg Zn Purpurin Amine NT2H2 in a mixed solvent composed of 5 ml water and 1 ml N,N-dimethyl formamide.

Dimer XV is produced by the method of Example 4 from a solution of 20 mg Purpurin II in 1.25 ml water and 0.8 ml N,N-dimethyl formamide, a solution of 20 mg 1-ethyl-3-(3-dimethylaminopropyl)-carbodiimide.HCl in 0.6 ml water, and a solution of 15 mg Chlorin Amine NT2H2 in a mixed solvent composed of 5 ml water and 1 ml N,N-dimethyl formamide.

Dimer XVI is produced by the method of Example 1 from 1 g hematoporphyrin diacetate and a solution of 1 g Zn Chlorin NT2H2 in 50 ml solvent composed of 50 percent v/v 0.2 molar aqueous sodium hydroxide and tetrahydrofuran.

An amine is produced from Chlorin NT2H2 (Zn Chlorin Amine NT2H2) by the method of the first paragraph of Example 3. Dimer XVII is then produced by the method of the second paragraph of Example 3 from a solution of 20 mg hematoporphyrin in 1.25 ml water and 0.8 ml N,N-dimethyl formamide, a solution of 20 mg 1-ethyl-3(3-dimethylaminopropyl)-carbodiimide.HCl in 0.6 ml water, and a solution of 15 mg Zn Chlorin Amine NT2H2 in a mixed solvent composed of 5 ml water and 1 ml N,N-dimethyl formamide.

Dimer XVIII is produced by the method of Example 4 from a solution of 20 mg Purpurin II in 1.25 ml water and 0.8 ml N,N-dimethyl formamide, a solution of 20 mg 1-ethyl-3-(3-dimethylaminopropyl)-carbodiimide.HCl in 0.6 ml water, and a solution of 15 mg Chlorin Amine NT2H2 in a mixed solvent composed of 5 ml water and 1 ml N,N-dimethyl formamide.

The nickel complex of Chlorin NT2H2 was also prepared by the method described in Example 7, except that nickel acetate was substituted for the zinc acetate. The nickel complex of Chlorin NT2H2 was found to have absorbance peaks in the visible spectrum at 405, 498, 533, 588 and 630 namometers ($\epsilon$ 145 779, 11 034, 8 693, 19 392, 64 146).

Dimer XIX is produced by the method of Example 1 from 1 g hematoporphyrin diacetate and a solution of 1 g Ni Chlorin NT2H2 in 50 ml solvent composed of 50 percent v/v 0.2 molar aqueous sodium hydroxide and tetrahydrofuran.

An amine (Ni Chlorin Amine NT2H2) is prepared from Ni Chlorin NT2H2 by the method of the first paragraph of Example 3. Dimer XX is then produced by the method of the second paragraph of Example 3 from a solution of 20 mg hematoporphyrin in 1.25 ml water and 0.8 ml N,N-dimethyl formamide, a solution of 20 mg 1-ethyl-3(3-dimethylaminopropyl)-carbodiimide.HCl in 0.6 ml water, and a solution of 15 mg Ni Chlorin Amine NT2H2 in a mixed solvent composed of 5 ml water and 1 ml N,N-dimethyl formamide.

Dimer XXI is produced by the method of Example 4 from a solution of 20 mg Purpurin II in 1.25 ml water and 0.8 ml N,N-dimethyl formamide, a solution of 20 mg 1-ethyl-3-(3-dimethylaminopropyl)-carbodiimide.HCl in 0.6 ml water, and a solution of 15 mg Ni Chlorin Amine NT2H2 in a mixed solvent composed of 5 ml water and 1 ml N,N-dimethyl formamide.

Figure 2:
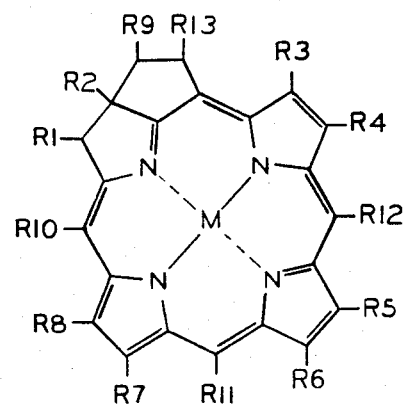
FIG. 2 is a structural formula for metal complexes of a family of chlorins from which dimers in accordance with the instant invention can be produced; in these complexes, an isocyclic ring which corresponds with the unsaturated isocyclic ring of the purpurins of FIG. 1 is saturated.

The zinc and nickel complexes of Chlorin NT2H2 have the formula of FIG. 2 of the drawings where R1 through R8 are ethyl, R9 is $CO_2CH_2CH_2$ and R10 through R13 are hydrogen. M is Zn for the zinc complex and Ni for the nickel complex.

EXAMPLE 9

Production of Purpurin NT2 and Purpurin NT1

A solution of 100 mg meso-(β-ethoxycarbonylvinyl-)octaethyl porphyrin in 20 ml glacial acetic acid was heated under reflux in air for 24 hours. The solution was allowed to stand at room temperature of about 22° until it cooled; the solvent was removed in vacuo; and the residue was dissolved in the minimum dichloromethane containing 1 percent v/v of methanol and chromatographed on silica. First and second major green bands were collected; the solvent was removed from the first band; and the crude product was dissolved in 4 ml dichloromethane containing 1 percent v/v of methanol and recrystallized, yielding 40 mg "Purpurin NT1", the compound having the formula of FIG. 7 of the drawings where R1 is $=CHCH_3$, R2 through R8 are ethyl, R9 is $CO_2CH_2CH_3$ and R10 through R13 are hydrogen. Purpurin NT1 was identified by nuclear magnetic resonance; it has absorbance peaks in the visible spectrum at wavelengths of 438, 510, 540, 583, 653, and 715 nanometers (ε 104 158, 9 450, 11 130, 15 540, 9 020, 42 629).

The solvent was also removed from the second green band, and the crude product was dissolved in 4 ml dichloromethane containing 1 percent v/v of methanol and recrystallized, yielding 39 mg Purpurin NT2, which was identified by nuclear magnetic resonance.

Purpurin NT1 was hydrogenated by a procedure similar to that described above in Example 8, yielding, after work-up and chromatographic purification as there described, 65 mg Chlorin NT2H2.

Dimer XXII is produced by the method of Example 1 from 1 g hematoporphyrin diacetate and a solution of 1 g Purpurin NT1 in 50 ml solvent composed of 50 percent v/v 0.2 molar aqueous sodium hydroxide and tetrahydrofuran.

An amine (Purpurin Amine NT1) is produced from Purpurin NT1 by the method of the first paragraph of Example 3. Dimer XXIII is then produced by the method of the second paragraph of Example 3 from a solution of 20 mg hematoporphyrin in 1.25 ml water and 0.8 ml N,N-dimethyl formamide, a solution of 20 mg 1-ethyl-3-(3-dimethylaminopropyl)-carbodiimide.HCl in 0.6 ml water, and a solution of 15 mg Purpurin Amine NT1 in a mixed solvent composed of 5 ml water and 1 ml N,N-dimethyl formamide.

Dimer XXIV is produced by the method of Example 4 from a solution of 20 mg Purpurin II in 1.25 ml water and 0.8 ml N,N-dimethyl formamide, a solution of 20 mg 1-ethyl-3-(3-dimethylaminopropyl)-carbodiimide.HCl in 0.6 ml water, and a solution of 15 mg Purpurin Amine NT1 in a mixed solvent composed of 5 ml water and 1 ml N,N-dimethyl formamide.

The procedure described in Example 6 has been used to produce other purpurins. Typical ones of the starting materials used and the intermediates and purpurins produced are set forth tabularly in Examples 10, 11 and 12.

EXAMPLE 10

| Compound | | Formula of |
|---|---|---|
| Starting material, | Nickel meso-formyletio porphyrin I | FIG. 6* |
| First Intermediate, | Nickel meso-(β-ethoxycarbonyl-vinyl)-etio porphyrin I | FIG. 6* |
| Second intermediate, | Meso-(β-ethoxycarbonylvinyl)-etio porphyrin I | FIG. 3* |
| "Purpurin ET2" | | FIG. 7* |

*Where: R1, R3, R5, and R7 are $CH_3$, R2, R4, R6, and R8 are $CH_2CH_3$. In the starting material, R is CHO and M is Ni. In the first intermediate, R is $CH=CHCO_2CH_2CH_3$ and M is Ni. In the second intermediate, R is $CH=CHCO_2CH_2CH_3$. In Purpurin ET2, R9 is $CO_2CH_2CH_3$ and R10 through R13 are hydrogen.

The production of nickel meso-formyletio porphyrin I is disclosed in a Journal article by Johnson et al., J. Chem. Soc. (c) 1966, p. 794.

EXAMPLE 11

| Compound | | Formula of |
|---|---|---|
| Starting Material | Nickel meso-formyl coproporphyrin I tetramethyl ester* | FIG. 6** |
| First intermediate, | Nickel meso-(β-ethoxycarbonyl-vinyl)coproporphyrin I tetramethyl ester | FIG. 6** |
| Second intermediate, | Meso-(β-ethoxycarbonylvinyl)-coproporphyrin I tetramethyl ester | FIG. 3** |
| "Purpurin JP1" | | FIG. 7** |

*Produced as subsequently described herein.
**Where: R1, R3, R5, and R7 are $CH_3$ and R2, R4, R6 and R8 are $CH_2CH_2CO_2CH_3$. In the starting material, R is CHO and M is Ni. In the first intermediate, R is $CH=CHCO_2CH_2CH_3$ and M is Ni. In the second intermediate, R is $CH=CHCO_2CH_2CH_3$. In Purpurin JP1, R9 is $CO_2CH_2CH_3$ and R10 through R13 are hydrogen.

The nickel meso-formyl coproporphyrin I tetramethyl ester starting material used in the procedure of Example 11 was produced from a commercially available material, coproporphyrin I tetramethyl ester (formula of FIG. 3 of the attached drawings); nickel coproporphyrin I tetramethyl ester was produced therefrom (formula of FIG. 6 where M is Zn). In both cases, R1, R3, R5 and R7 are $Ch_3$ and R2, R4, R6 and R8 are $CH_2CH_2CO_2CH_3$.

The Ni Coproporphyrin I Tetramethyl ester was prepared from a solution of 100 mg coproporphyrin I tetramethyl ester in a mixed solvent composed of 50 ml dichloromethane and 5 ml methanol and 100 mg nickel acetate. A mixture which was prepared by adding the nickel acetate to the solution was refluxed for about 12 hours until the electronic spectrum of the reaction mixture indicated that chelation was complete. The reaction mixture was then concentrated to 7 ml and allowed to cool to room temperature of about 22°. Product which precipitated was recovered by filtration, dissolved in a mixed solvent composed of 5 ml dichloromethane and 2 ml methanol, and recrystallized, yielding 98 mg Ni coproporphyrin I tetramethyl ester. The compound showed absorbance peaks in the visible spectrum at 392, 515 and 552 nanometers; the relative intensities at these peaks were 20.19, 1 and 2.56, respectively.

The Nickel-meso-formyl coproporphyrin I tetramethyl ester was prepared from the following materials: 2.8 ml freshly distilled phosphorus oxychloride, 2 ml dry dimethyl formamide, a solution of 100 mg nickel-coproporphyrin I tetramethyl ester in 75 ml dry 1,2-dichloromethane and 75 ml saturated aqueous sodium acetate. The dimethyl formamide was cooled on an ice bath, and the phosphorus oxychloride was added thereto dropwise. The solution which resulted was allowed to stand at room temperature for 30 minutes, and was then warmed to 50°. The nickel-coproporphyrin I tetramethyl ester solution was then added dropwise, with stirring, to the phosphorus oxychloride solution; the addition was made over a period of 30 minutes. The reaction mixture was maintained at about 50°, with stirring, for an additional 2 hours, during which time a change in color from red to green was observed. The sodium acetate solution was then added to the reaction mixture, and stirring was continued for an additional 2 hours. The organic and the aqueous phases were then separated, and the aqueous phase was extracted with dichloromethane. The organic phase and the dichloromethane extract were then combined, and evaporated to dryness. The solid which remained was recrystallized from a solvent composed of equal parts by volume of dichloromethane and methanol, yielding 86 mg red microcrystals which were identified by nuclear magnetic resonance as nickel-mesoformylcoproporphyrin I tetramethyl ester. Absorbance peaks were found in the visible spectrum at 400, 420, 558 and 645 nanometers, with relative intensities of 10.10, 8.69, 1.02 and 1, respectively.

EXAMPLE 12

| Compound | | Formula of |
|---|---|---|
| Starting Material, | Nickel meso-formyloctaethylporphyrin | FIG. 6* |
| First intermediate, | Nickel meso-(β-methoxycarbonylvinyl)octaethylporphyrin | FIG. 6* |
| Second intermediate, | Meso-(β-methoxycarbonylvinyl)-octaethylporphyrin | FIG. 3* |
| "Purpurin GG2" | | FIG. 7* |

*Where: R1 through R8 are $CH_2CH_3$. In the starting material, R is CHO and M is Ni. In the first intermediate, R is $CH=CHCO_2CH_3$ and M is Ni. In the second intermediate, R is $CH=CHCO_2CH_3$. In Purpurin GG2, R9 is $CO_2CH_3$ and R10 through R13 are hydrogen.

The procedure of Example 8 has been used to hydrogenate Purpurin ET2 and Purpurin JP1, producing Chlorin ET2H2 and Chlorin JP1H2, respectively, where the isocyclic ring (to which the R9 substituent is attached) is saturated. The chlorins had the same substituents as the starting purpurins, but the structure of FIG. 8 instead of that of FIG. 7.

Data concerning use of the Example 8 procedure to produce other complexes are set forth below:

| Starting Purpurin or Chlorin | Zinc or nickel Compound | Complex Produced |
|---|---|---|
| Purpurin ET2 | Zinc acetate | Zn |
| Purpurin ET2 | Nickel acetate | Ni |
| Purpurin GG2 | Zinc acetate | Zn |
| Purpurin GG2 | Nickel acetate | Ni |
| Chlorin ET2H2 | Zinc acetate | Zn |
| Chlorin ET2H2 | Nickel acetate | Ni |

Additional peak absorbance data (visible spectrum, wavelengths in nanometers) are given below.

| Compound | Wavelengths (relative intensities) |
|---|---|
| Purpurin ET2 | 406(16.69), 424(15.26), 502(1.36) 531(1), 566(1.5), 695(3.47) |
| Chlorin ET2H2 | 400(70.16), 498(5.53), 530(1.29), 555(1), 606(1.91), 662(20.82) |
| Zn Chlorin ET2H2 | 401(20.36), 530(1), 568(1.18), 630(3.20) |
| Purpurin ET2 | 434(16.44), 530(1), 576(1.31) 612(1.77), 660(5.0) |
| Ni Purpurin ET2 | 434(5.14), 657(1) |
| Ni Chlorin ET2H2 | 404(11.70), 497(1), 622(4.41) |
| Purpurin JP1 | 409(22.41), 504(1.67), 541(1.21) 567(1.08), 647(1), 691(3.79) |
| Chlorin JP1H2 | 401(14.53), 650(1) |
| Purpurin GG2 | 406(12.94), 427(19.18), 500(1), 526(1), 565(1.89), 637(0.76), 695(5.25) |
| Zn Purpurin GG2 | 436(8.33), 616(1), 661(3.43) |
| Ni Purpurin GG2 | 427(4.20), 648(1) |

Dimers according to the invention are produced from various ones of the foregoing purpurins, and purpurin complexes by the methods of Examples 1, 3 and 4. Typical ones of the starting materials used, the examples which describe the procedures and the dimers produced are identified in the following table:

| Starting Materials | | Procedure of Example | Dimer |
|---|---|---|---|
| First | Second | | |
| HpDA[1] | Purpurin ET2 | 1 | XXV |
| Hp[2] | Purpurin ET2 | 3 | XXVI |
| PurII[3] | Purpurin ET2 | 4 | XXVII |
| HpDA | Purpurin JP1 | 1 | XXVIII |
| Hp | Purpurin JP1 | 3 | XXIX |
| PurII | Purpurin JP1 | 4 | XXX |
| HpDA | Purpurin GG2 | 1 | XXXI |
| Hp | Purpurin GG2 | 3 | XXXII |
| PurII | Purpurin GG2 | 4 | XXXIII |
| HpDA | Zn Purpurin GG2 | 1 | XXXIV |
| Hp | Zn Purpurin GG2 | 3 | XXXV |
| PurII | Zn Purpurin GG2 | 4 | XXXVI |
| HpDA | Ni Purpurin GG2 | 1 | XXXVII |
| Hp | Ni Purpurin GG2 | 3 | XXXVIII |
| PurII | Ni Purpurin GG2 | 4 | XXXIX |
| HpDA | Ni Purpurin ET2 | 1 | XL |
| Hp | Ni Purpurin ET2 | 3 | XLI |
| PurII | Ni Purpurin ET2 | 4 | XLII |
| HHpDA | Zn Purpurin ET2 | 1 | XLIII |
| Hp | Zn Purpurin ET2 | 3 | XLIV |
| PurII | Zn Purpurin ET2 | 4 | XLV |

[1] Hematoporphyrin diacetate
[2] Hematoporphyrin
[3] Purpurin II

In the foregoing table, and in the following table:

(1) where the procedure of Example 1 is used, the second starting material is in a solution of sodium hydroxide and tetrahydrofuran;

(2) where the procedures of Examples 3 and 4 are used, an amine is produced from the second starting material by the method of the first paragraph of Example 3 and that amine is then used in carrying out the method of the second paragraph of Example 3 and the method of Example 4;

(3) where the procedure of the second paragraph of Example 3 is used, the Hp is dissolved in water and N,N-dimethyl formamide and this solution is added to a carbodiimide hydrochloride solution before a solution of the amine of the second starting material is added; and (4) where the procedure of Example 4 is used, the PurII is dissolved in water and N,N-dimethyl formamide and this solution is added to a carbodiimide hydrochloride solution before a solution of the amine of the second starting material is added.

Dimers according to the invention are also produced from various ones of the foregoing chlorins and chlorin complexes by the methods of Examples 1, 3 and 4. Typical ones of the starting materials used, the examples which describe the procedures and the dimers produced are identified in the following table:

| Starting Materials | | Procedure of | |
|---|---|---|---|
| First | Second | Example | Dimer |
| HpDA | Zn Chlorin ET2H2 | 1 | XLVI |
| Hp | Zn Chlorin ET2H2 | 3 | XLVII |
| PurII | Zn Chlorin ET2H2 | 4 | XLVIII |
| HpDA | Ni Chlorin ET2H2 | 1 | IL |
| Hp | Ni Chlorin ET2H2 | 3 | L |
| PurII | Ni Chlorin ET2H2 | 4 | LI |
| HpDA | Chlorin ET2H2 | 1 | LII |
| Hp | Chlorin ET2H2 | 3 | LIV |
| PurII | Chlorin ET2H2 | 4 | LV |
| HpDA | Chlorin JP1H2 | 1 | LVI |
| Hp | Chlorin JP1H2 | 3 | LVII |
| PurII | Chlorin JP1H2 | 4 | LVIII |

In vitro and in vivo testing of purpurins and chlorins produced as described in Examples 6 through 12 was also carried out, some being described in application Ser. No. 842,125. For the in vitro testing, the compounds were dissolved in dimethyl sulfoxide or in a solvent that is commercially available under the trade designation PROTOSOLV, and diluted with phosphate buffer saline to a concentration of 0.010 mg per ml. The tests were conducted on FANFT (N-[4-(5-nitro-2furyl)2-thiazolyl] formamide) induced rat bladder tumor cells. Two tests were conducted, uptake and toxicity.

The uptake test involved incubating the FANFT induced rat bladder tumor cells with a solution of a purpurin or with a solution of a chlorin at a concentration of 0.010 mg per ml for one hour, temperature 37°, followed by removal of the incubation media, three washes of the cells with phosphate buffered saline, and extracting and quantitating of the purpurin or chlorin retained by the cells. The procedure as used in investigating the use of HpD in rat tumor cells is described in detail in a journal article by Garbo et al., Analytical Biochemistry, Vol. 151 (No. 1), pp. 70–81, 1985.

The toxicity test involved the incubation and washing steps of the uptake test, followed by illumination of the cells with red light of a wavelength greater than 590 nanometers. Cell survival was then determined by Trypan Blue exclusion, a technique described in a journal article by Schneck, R., Arch. Path. (Lab. Med.) 35, p. 857, 1943.

The uptake test was positive for Purpurin NT2 and for Chlorin NT2H2. The results of the toxicity test are given in the following table, together with the results of toxicity testing of HpD, of phosphate buffer saline and of the solvent system in which the purpurin of chlorin was dissolved.

| Test Solution | Average Viability |
|---|---|
| Purpurin NT2 | 46 |
| Chlorin NT2H2 | 51 |
| HpD | 42 |
| Phosphate buffer saline | 93 |
| Mixed solvent | 96 |

The in vivo testing was conducted on male Fisher 344 rats weighing 135 to 150 g in whom the transplantable FANFT (N-[4-(5-nitro-2-furyl)-2-thiazolyl]formamide tumor system had been implanted. (Use of this system is reported by Selman, S. H., et al., Cancer Research, pp. 1924–1927, May, 1984.) Two tumors were implanted into the subcutaneous tissue of the abdominal wall of each test animal; when the testing was carried out, each tumor was about 1 cm in diameter.

The purpurins and chlorins tested were dissolved in a commercially available non-ionic solubilizer and emulsifier obtained by reacting ethylene oxide with castor oil in a ratio of 35 moles of ethylene oxide per mole of castor oil, diluting the resulting solution with 1,2-propanediol, and producing an emulsion with the resulting solution and 0.9 percent w/w aqueous sodium chloride solution. The specific non-ionic solubilizer used is available from BASF under the designation CREMOPHOR EL; it is composed of fatty acid esters of polyglycols, glycerol polyglycols, polyethylene glycols and ethoxylated glycerol. The test solutions were prepared from 50 mg purpurin of chlorin, 1 or 2 ml warm solubilizer (enough to dissolve the test compound), enough 1,2-propanediol to make a solution of the purpurin or chlorin in a mixed diol/solubilizer solvent containing 32.9 percent w/w solubilizer; finally, enough 0.9 percent w/w aqueous sodium chloride was added to make 10 ml test solution so that the final concentration of the purpurin or chlorin in the test solution was 5 mg per ml. Each test solution was made, with mechanical shaking and stirring, by dissolving the purpurin or chlorin in the solubilizer, diluting the resulting solution with the indicated amount of 1,2-propanediol, and adding the sodium chloride solution to the diluted solution. A control solution was also prepared for use with each test solution. The control was identical with the test solution except that it contained no purpurin or chlorin. The test solutions were prepared in air, but it is believed that a nitrogen atmosphere would be advantageous because it would minimize the chance of a reaction with oxygen.

The testing involved injecting each rat with a solution of the purpurin or chlorin under test, dosage 4 mg purpurin or chlorin per kg of body weight or 10 mg purpurin or chlorin per kg of body weight or with the same volume of the appropriate control, irradiating one of the two tumors with light for 30 minutes, sacrificing the animals, and examining the tumors. The injections were made via the dorsal tail vein. The irradiation of one of the tumors occurred twenty four hours after each rat was injected while the other of the two tumors was shielded by an opaque box.

Tumor temperature and body core temperature were monitored, using thermistors, one placed into the tumor and one placed intrarectally. Tumor temperature was kept within 2° of body core temperature by directing a jet of cool air over the tumor.

The light source was a slide projector that had a 500 watt bulb fitted with a red filter which is available from Corning Glass Works under the designation 2418. The light was reflected 90° by a silvered mirror, and was focused onto the tumor with a secondary condensing lens. The light intensity on the tumor was monitored, using a photometer/radiometer that is available from United Detector Technology under the designation "UDT #351", and was maintained at 200 mw per $cm^2$.

Six rats were injected with the purpurin or chlorin test solution and two were injected with the appropriate control solution.

Four hours after the irradiation, three of the rats that had been injected with the test solution and one of the rats that had been injected with the control were sacrificed by an intracardiac injection of saturated aqueous potassium chloride solution. Twenty four hours after the irradiation, another three of the rats that had been injected with the test solution and the other rat that had been injected with the control were sacrificed in the same way. During the testing, the rats were under barbituate anesthesia (65 mg per kg body weight).

The tumors were then excised, placed in 10 percent w/w phosphate-buffered formalin and cut into three sections perpendicular to their long axis. The tumors were then embedded in paraffin and cut into sections five microns in width. The sections were stained with hematoxylin and eosin.

Histologic examination of the stained sections revealed approximately comparable areas of hemorrhage and tumor cell necrosis in specimens removed four hours after irradiation from animals that had been injected with Purpurin NT2, with Purpurin GG2, and with ET2. However, tumor cells which appeared to be viable were observed. Only minor hemorrhage and tumor cell necrosis were observed in specimens removed four hours after irradiation from animals that had been injected with Purpurin JP1 but much greater hemorrhage and necrosis were observed in specimens that had been injected with Purpurin ZnET2 and even more in specimens that had been injected with Chlorin SnET2H2. Tumor necrosis was extensive in specimens removed twenty four hours after irradiation from animals that had been injected with Purpurin NT2, with Purpurin GG2, with Purpurin ET2, with Purpurin JP1, with Purpurin ZnET2 and with Chlorin SnET2H2; no viable tumor cell was observed in specimens from animals that had been injected with Purpurin ZnET2 and Chlorin SnET2H2, while a few were observed in specimens from animals that had been injected with Purpurin NT2 and with Purpurin ET2, and more were observed in specimens from animals that had been injected with Purpurin GG2 and with Purpurin JP2. No change in the tumors was observed in the specimens that were removed from animals that had been injected with the control solution. Tumor necrosis was complete in specimens removed from animals that had been injected with purpurin NT1 both four hours after irradiation and twenty four hours after irradiation. However, the irradiation was found to have caused extensive liver damage to some of the animals. The liver damage is believed to have occurred because there was residual Purpurin NT1 in the liver which was unintentionally irradiated. The in vivo testing, however, indicated that Purpurin NT1 is highly effective when properly used.

The in vivo test procedure described above has also been used to evaluate solutions in which the Purpurin NT2, Purpurin GG2, Purpurin NT1, Purpurin JP1, Purpurin ET2, Purpurin ZnET2 and Chlorin SnET2H2 were replaced by Chlorin NT2H2 and by Chlorin ET2H2. Histologic examination of the stained sections from rats into which the Chlorin NT2H2 and ET2H2 solutions had been injected indicated that these chlorins were substantially equivalent in this test and were similar to Purpurin NT2, to Purpurin GG2 and to Purpurin ET2, the only difference observed being that hemorrhage within the tumors was less pronounced with the chlorins.

It will be appreciated from the results reported above in Example 9 that the cyclization step of Example 1 by which Purpurin II and Purpurin III are produced could be carried out in air, rather than in nitrogen, and that the reaction product would then be a mixture of Purpurin II, Purpurin III, and the following purpurins:

| Compound | Structure (referring to attached drawings) |
|---|---|
| Purpurin XXI | FIG. 9: R1 is =CHCH$_3$<br>R2-R5, R7 and R8 are CH$_2$CH$_3$<br>R9 is CO$_2$CH$_2$CH$_3$ |
| Purpurin XXII | FIG. 13 R1 is =CHCH$_3$<br>R2-R6 and R8 are CH$_2$CH$_3$<br>R9 is CO$_2$CH$_2$CH$_3$ |

In fact, cyclization in air can be used to produce purpurins, and metal complexes can be produced from those purpurins by the method of Example 7, with or without the modifications thereof subsequently described herein, where the purpurins and complexes have the structures of FIGS. 10-12, of FIGS. 14-18, of FIGS. 29-33, of FIGS. 34-38, of FIGS. 44-48 and of FIGS. 54-58. In all cases, a mixture of products will be produced, some in which R1 is saturated and some in which R1 is a bivalent aliphatic hydrocarbon radical having from 2 to 4 carbon atoms wherein both of the valences of the radical are attached to the same carbon atom thereof and to a carbon atom of the purpurin or metal complex. Furthermore, after cleavage of the exocyclic ring of FIGS. 9-18, oxidation in air can be used, in the purpurins and complexes of FIGS. 29-33 and of FIGS. 44-48 to convert R2 to a bivalent aliphatic hydrocarbon radical having from 2 to 4 carbon atoms wherein both of the valences of the radical are attached to the same carbon atom thereof and to a carbon atom of the purpurin or metal complex. In general, purpurins can be converted to the corresponding chlorins by the hydrogenation method described in Example 8; chlorins can be converted to the corresponding purpurins by oxidation; and chlorin metal complexes can be produced from chlorins by the method of Example 7, with or without the modifications thereof subsequently described herein. However, hydrogenation of Purpurin NT1 (where there was a double bond between the R1 substituent and a carbon of the purpurin), as described in Example 9, produced Chlorin NT2H2 (where both the double bond of the exocyclic ring and that of R1 were saturated). It will be appreciated that the R1 double bond forms in the Example 9 procedure because a hydroxyl group is introduced into the molecule and, at the temperature of reflux, the elements of water are eliminated to form the double bond. Elimination of the elements of water can be prevented in the Example 9 procedure, or, more generally, whenever R1 is to be bivalent, by cyclizing at a lower temperature; the resulting purpurin can then be hydrogenated to the corresponding chlorin and the double bond with R1 can be formed by heating.

The method of Example 7, supra, can be used to produce metal complexes of other purpurins and of various chlorins. Specifically, an equivalent amount of another purpurin or of a chlorin can be substituted for the Purpurin NT2, or copper acetate, nickel acetate, cobalt acetate, silver acetate, palladium acetate, or platinum acetate can be substituted for the zinc acetate, or both substitutions can be made. In this manner, purpurin metal complexes having the formulas of FIGS. 54-58 where M is one of the metals named above in this paragraph can be produced from purpurins having the formulas of FIGS. 34-38; chlorin metal complexes having the formulas of FIGS. 49-53 where M has the same meaning can be produced from chlorins having the formulas of FIGS. 39–43; purpurin metal complexes having the formulas of FIGS. 44–48 where M has the indicated meaning can be produced from purpurins having the formulas of FIGS. 29–33; metal complexes of purpurins having the formulas of FIGS. 9–18 can be produced; metal complexes having the structure of FIG. 1 can be produced from purpurins having the structure of FIG. 7; and metal complexes having the structure of FIG. 2 can be produced from chlorins having the structure of FIG. 8. Other complexes can be produced by the method of Example 7 from salts containing cations other than acetate, and producing complexes which have the structures of the Figs. to which reference is made above in this paragraph, but where M does not represent merely a metal anion. Examples of salts that can be substituted for zinc acetate in the Example 7 procedure are identified below, together with the identity of M in the foregoing Figs.:

| Salt | Identity of M |
|---|---|
| $FeCl_3$ | $Fe(Cl)$ |
| $MnCl_4$ | $Mn(Cl)$ |
| $InCl_3$ | $In(Cl)$ |
| $VCl_4$[1] | $V(O)$ |
| $Tl(CF_3CO_2)_3$ | $Tl(OAc)(H_2O)$ |
| $SnCl_2$ | $Sn(OH)_2$ |
| $[Rh(CO)_2Cl]_2$ | $Rh(Cl)(H_2O)$ |

[1]Using phenol as the solvent instead of glacial acetic acid.

The procedure of Example 7 can also be modified by substituting phenol for glacial acetic acid and metal chelates of pentane, 2,4-dione for zinc acetate to produce complexes of any of the foregoing purpurins and chlorins. Metals that can be so reacted (as pentane, 2,4-dione chelates) and the identity of M in the complex that is produced are set forth in the following table:

| Metal | Identity of M | Metal | Identity of M |
|---|---|---|---|
| Al | Al(acac)[1] | Th | Th(acac)$_2$ |
| Sc | Sc(acac) | U | U(acac)$_2$ |
| Ga | Ga(acac) | La | La(acac$_2$) |
| In | In(acac) | Ce | Ce(acac) |
| Mo | Mo(acac) | Nd | Nd(acac) |
| Ti | Ti(acac)$_2$ | Sm | Sm(acac) |
| Zr | Zr(acac)$_2$ | Gd | Gd(acac) |
| Hf | Hf(acac)$_2$ | Tb | Tb(acac) |
| Eu | Eu(acac) | Dy | Dy(acac) |
| Pr | Pr(acac) | Ho | Ho(acac) |
| Yb | Yb(acac) | Er | Er(acac) |
| Y | Y(acac) | Tm | Tm(acac) |
| Lu | Lu(acac) | | |

[1]The pentane, 2,4-dione portion of a chelate thereof with a metal.

Complexes of any of the foregoing purpurins and chlorins can also be produced by the procedure of Example 7, substituting dimethylformamide for glacial acetic acid and $CrCl_2$ for zinc acetate. Metal complex formation occurs at higher temperatures when dimethylformamide is used, because of its higher boiling temperature. M in the complexes is Cr(OH).

Similarly, complexes of the foregoing purpurins and chlorins can be produced by the procedure of Example 7, substituting pyridine for glacial acetic acid and $PbCl_2$ for zinc acetate. M in the complexes is Pb.

Figure 8:
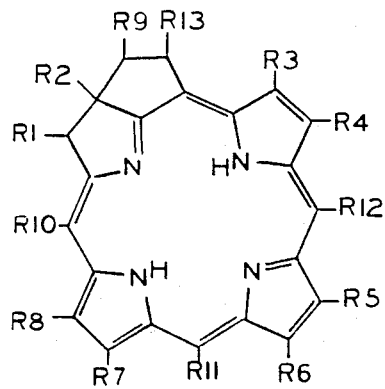
FIG. 8 is a structural formula for the family of chlorins having the structure of the complexes of FIG. 2; dimers according to the instant invention can be produced from these chlorins.

The method of Example 7 and the modifications thereof described above can be used to produce purpurin complexes having the structures of FIGS. 44–48 from purpurins having the structures of FIGS. 29–33; to produce chlorin complexes having the structures of FIGS. 49–53 from chlorins having the structures of FIGS. 39–43; to produce purpurin complexes having the structures of FIGS. 54–58 from purpurins having the structures of FIGS. 34–38; to produce purpurin complexes from purpurins having the structure of FIG. 7; and to produce chlorin complexes of FIG. 2 from chlorins having the structure of FIG. 8.

Figure 19:
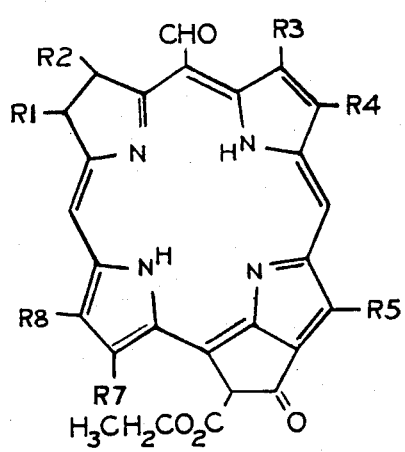
Figure 24:
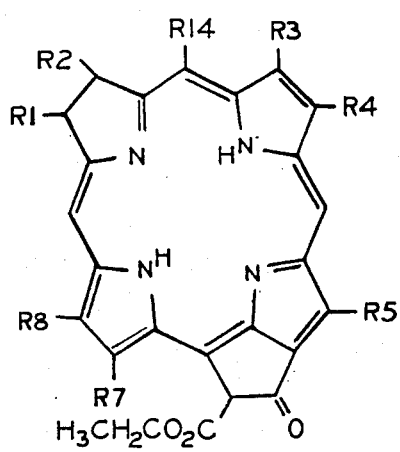
Figure 29:
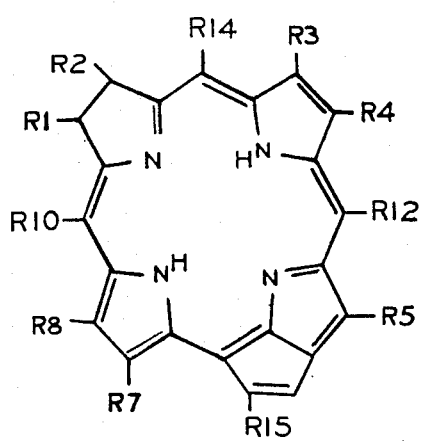

The following example illustrates the production of Chlorin I, a compound having the structure of FIG. 19 where R1–R5, R7 and R8 are $CH_2CH_3$, Chlorin II, a compound having the structure of FIG. 24 where R1–R5, R7 and R8 are $CH_2CH_3$ and R14 is $CH_3$, and Purpurin XXIII, a compound having the structure of FIG. 29 where R1–R5, R7 and R8 are $CH_2CH_3$, R10 and R12 are H, R14 is $CH_3$ and R15 is $CO_2CH_2CH_3$.

EXAMPLE 13

Production of Chlorin I and Chlorin II

A 5 percent w/w solution of 100 mg Purpurin IV in dichloromethane containing 25 percent v/v methanol is caused to react by vigorous stirring in air while illuminated with visible light. The reaction is continued, with periodic monitoring by visible light spectroscopy, until the spectrum indicates that no Purpurin IV remains in the solvent. The dichloromethane/methanol solvent is then evaporated; a 4 ml portion of a 5 percent w/w solution of sodium methoxide in methanol is mixed with the residue and refluxed for 2 hours; and the solution is cooled. A 5 ml portion of water is then mixed with the reaction product; an organic layer which forms is separated from the aqueous layer and treated in vacuo to remove solvent; and the crude product which remains is dissolved in about 3 ml dichloromethane containing 1 percent v/v methanol and chromatographed on silica gel. Chlorin II is then produced by reducing the CHO group of Chlorin I to $CH_3$, e.g., using the hydrogenation method of Example 8.

Production of Purpurin XXIII

A solution of 60 mg sodium borohydride in 10 ml methanol is added dropwise to a solution of 200 mg Chlorin II in 5 ml dichloromethane; the resulting solution is stirred at room temperature of about 22° for 2 hours, and is poured into 100 ml water. The organic phase is separated from the aqueous phase; the solvent is removed from the organic phase; and the solvent is evaporated. The residue is dissolved in 50 ml chloroform containing 25 percent v/v methanol; a 10 mg addition of p-toluene sulfonic acid is made; and the reaction mixture is refluxed for 6 hours. Water is then added to the reaction mixture; the organic layer is collected; and the solvent is removed by evaporation. The residue is dissolved in 5 ml dichloromethane containing 2 percent v/v methanol, the resulting solution is chrmatographed on silica gel; and Purpurin XXIII is recovered by evaporating the solvent from the chromatographed solution.

The procedure of Example 1 is used to produce dimers of Chlorin I, of Chlorin II and of Purpurin XXIII. The procedure of the first paragraph of Example 3 is used to produce amines of these compounds and the procedures of the second paragraph of Example 3 and of Example 4 are then used to produce dimers of the amines.

Figure 20:
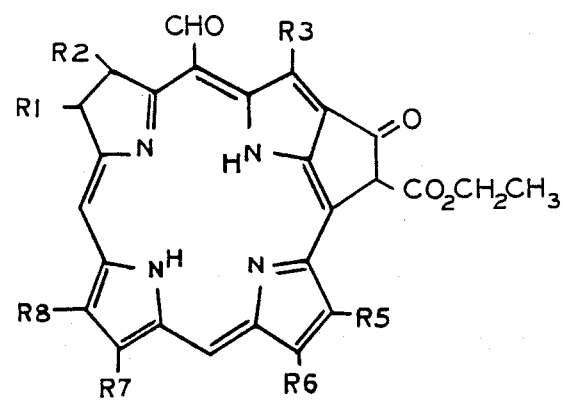
Figure 25:
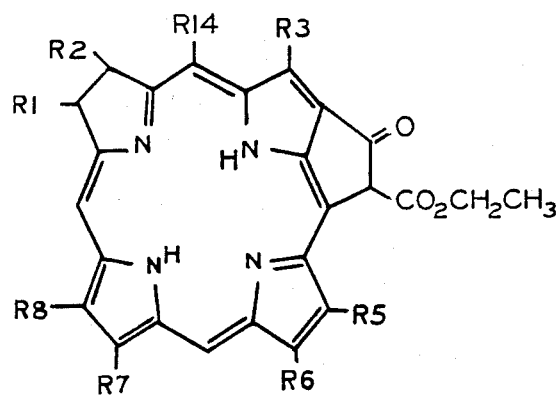
Figure 30:
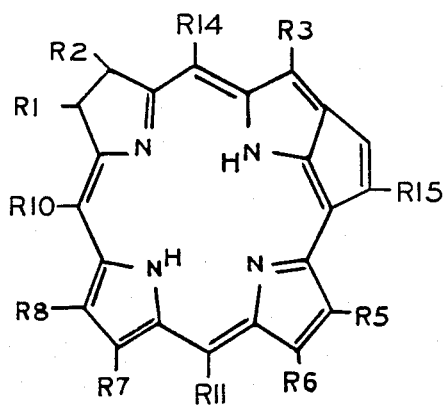

The procedure of Example 13 can also be used to produce other chlorins and other purpurins. For example, Purpurin XI can be substituted for Purpurin IV and Chlorin III, Chlorin IV and Purpurin XXIV can then be produced by the method of Example 13; these compounds are identified in the following table:

| Compound | Structure (referring to attached drawings) | |
|---|---|---|
| Chlorin III | FIG. 20: | R1-R3 and R5-R8 are $CH_2CH_3$ |
| Chlorin IV | FIG. 25: | R1-R3 and R5-R8 are $CH_2CH_3$ |
|  |  | R14 is $CH_3$ |
| Purpurin XXIV | FIG. 30: | R1-R3 and R5-R8 are $CH_2CH_3$ |
|  |  | R10 and R11 are H |
|  |  | R14 is $CH_3$ |
|  |  | R15 is $CO_2CH_2CH_3$ |

Similarly, Purpurin XVI can be substituted for Purpurin IV and Chlorin V, Chlorin VI and Purpurin XXV can then be produced by the method of Example 13; in all of these compounds R1-R3 and R5-R7 are $CH_2CH_3$. In Chlorin IV and Purpurin XXIV, R14 is $CH_3$, and in Purpurin XXIV R15 is $CO_2CH_2CH_3$.

Figure 22:
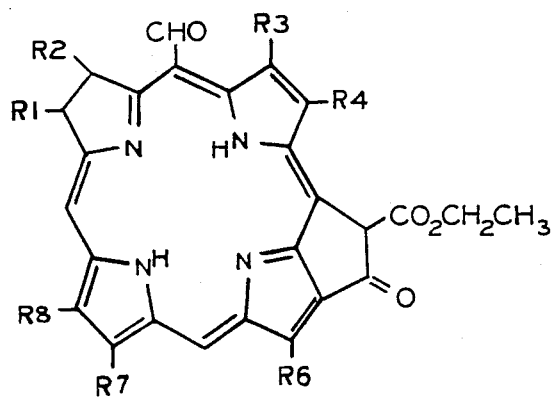
Figure 27:
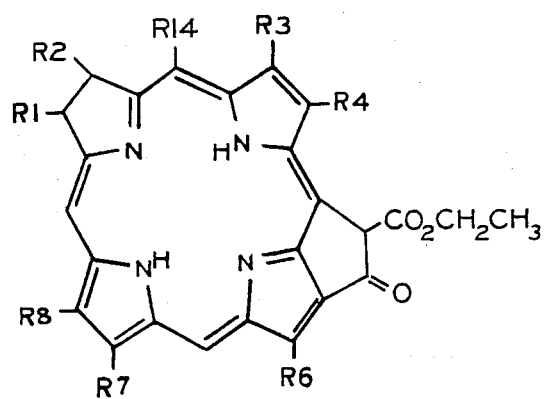
Figure 32:
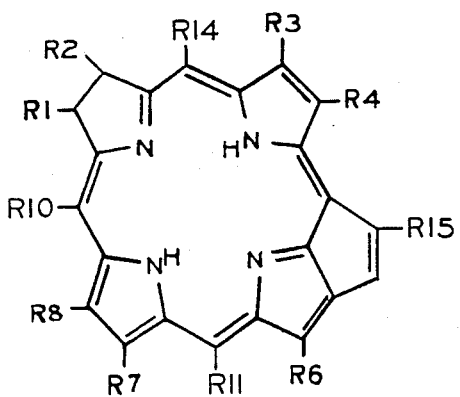

In a like manner, Purpurin XIX can be substituted for Purpurin IV and Chlorin VII, Chlorin VIII and Purpurin XXVI can then be produced by the method of Example 13; these compounds are identified in the following table:

| Compound | Structure (referring to attached drawings) | |
|---|---|---|
| Chlorin VII | FIG. 22: | R1-R4 and R6-R8 are $CH_2CH_3$ |
| Chlorin VIII | FIG. 27: | R1-R4 and R6-R8 are $CH_2CH_3$ |
|  |  | R14 is $CH_3$ |
| Purpurin XXVI | FIG. 32: | R1-R4 and R6-R8 are $CH_2CH_3$ |
|  |  | R10 and R11 are H |
|  |  | R14 is $CH_3$ |
|  |  | R15 is $CO_2CH_2CH_3$ |

Figure 23:
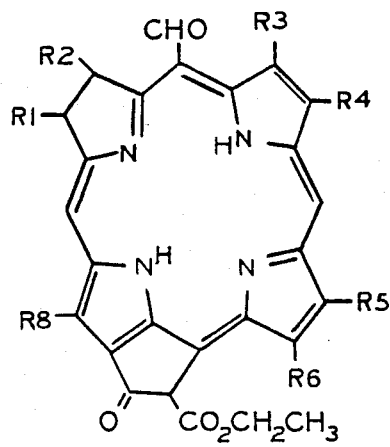
Figure 21:
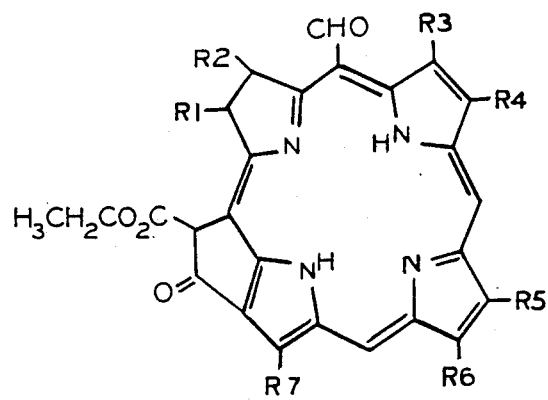
Figure 28:
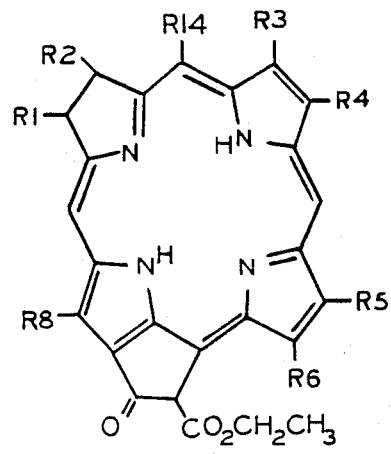
Figure 26:
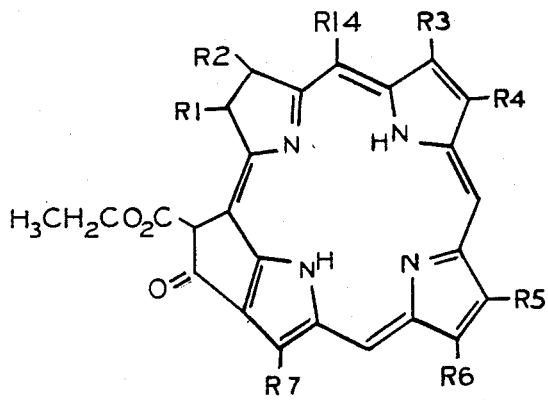
Figure 33:
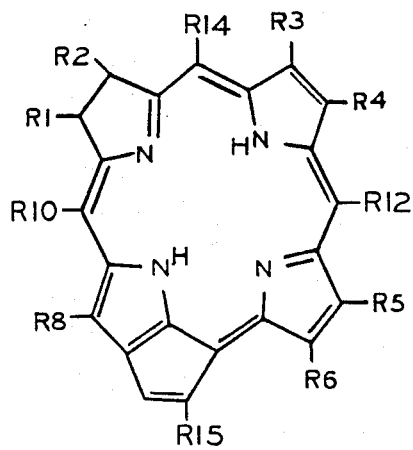
Figure 31:
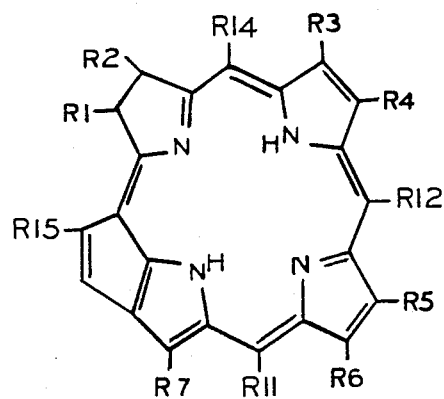

Finally, Purpurin VII can be substituted for Purpurin IV and Chlorin IX, Chlorin X and Purpurin XXVII can then be produced by the method of Example 13; these compounds are identified in the following table:

| Compound | Structure (referring to attached drawings) | |
|---|---|---|
| Chlorin IX | FIG. 23: | R1-R6 and R8 are $CH_2CH_3$ |
| Chlorin X | FIG. 28: | R1-R6 and R8 are $CH_2CH_3$ |
|  |  | R14 is $CH_3$ |
| Purpurin XXVII | FIG. 33: | R1-R6 and R8 are $CH_2CH_3$ |
|  |  | R10 and R12 are H |
|  |  | R14 is $CH_3$ |
|  |  | R15 is $CO_2CH_2CH_3$ |

Dimers according to the invention are also produced from Chlorin III, Chlorin IV, Chlorin V, Chlorin VI, Chlorin VII, Chlorin VIII, Chlorin IX and Chlorin X, and from Purpurin XXIV, Purpurin XXV, Purpurin XXVI and Purpurin XXVII, using the procedure of Example 1. Amines are also produced from these compounds using the procedure of the first paragraph of Example 3, and dimers are produced from the amines using the procedures of the second paragraph of Example 3 and of Example 4.

It will be appreciated that the purpurins that can be produced by the methods of the foregoing examples, and the chlorins that can be produced from those purpurins by the hydrogenation method of Example 8, have seven substituents which are present in the porphyrin starting materials from which the purpurins are produced. These are seven of the eight R1-R8 substituents, all but R6 in the purpurins of FIG. 34, all but R4 in the purpurins of FIG. 35, etc. The identities of these substituents depend on the identities of their pyrrole-, dipyrromethane-, and porphyrin-precursors. At least as initially produced, each purpurin also has an R9 substituent, and R15 substituent, or both; as is explained above, the identities of these substituent are determined by the identities of their porphyrin precursors. In addition, the purpurins of FIGS. 29-33 have the potential for substitution at R14, which is formyl when the purpurins are first produced, as described above, and can be reduced to methyl, as also described above, or to any other desired substituent by the reactions about to be described to which a formyl group introduced as R10, R11, R12, R13 or R16 can be subjected. Finally, each purpurin has additional sites for potential substitution, a plurality of R10, R11, R12, R13 and R16 (see FIGS. 34-38) substitutions being possible, which ones depending on the position of an exocyclic ring to which R15 and R16 are attached; as the purpurins are produced, there is hydrogen in each of these positions. A formyl group can be introduced by reaction with the Vilsmier reagent as the lowest of R10, R11 and R12, as R13 and as R16 (in the compounds of FIGS. 34-38), or the unsaturated exocyclic ring or rings can be saturated by hydrogenation (see procedure of Example 8, supra) and the formyl group can then be introduced as the lowest of R10, R11 and R12. The formyl group, after separation of isomers, if necessary, can be reduced to $CH_3$, or can be reduced to $CH_2OH$ or converted to an oxime group, which can then be converted to a cyano group, which, in turn, can be converted to an amide. The formyl group can also be reacted with Wittig reagents to give alkyl, alkenyl or carboxy side chains or to introduce the previously identified substituents which have an amine or an alcoholic OH function as the lowest of R10, R11 and R12, as R13 or as R16. After the desired group has been introduced as the lowest of R10, R11 and R12, as R13, as R16, or as some combination, the purpurin can be reacted in the same way to introduce a desired group as R11, if present. Finally, the chemistry can be used to introduce a desired group as R12, if present. Chlorins can be produced from purpurins having the structures of FIGS. 34-38 by the hydrogenation method of Example 8, and complexes can be made from those chlorins by the method of Example 7 and the previously discussed variations thereof.

In general, a dimer according to the instant invention can be made by the method of Example 1 from any of the foregoing purpurins, chlorins, purpurin complexes and chlorin complexes. Similarly, amines can be produced from any of the purpurins, chlorins or complexes, using the method of the first paragraph of Example 3, and dimers according to the instant invention can be made from the amines, using the procedures of the second paragraph of Example 3 and of Example 4. In addition, when the purpurin, chlorin or complex has a $CO_2CH_3$ group, a $CO_2CH_2CH_3$ or the like group in its structure, whether as R9 or 15 from the original ring closure, or in another position, a dimer can be produced by the method of Example 2 by reaction thereof with Purpurin Alcohol II, or with another purpurin alcohol produced by the method of Example 2, or with a chlorin alcohol produced by that method, or with an alcohol of a purpurin or chlorin metal complex produced by that method. Free carboxyl groups on purpurins, chlorins or complexes are capable of competing in the reactions of the Example 1 through 4 procedures for preparing dimers according to the instant invention.

As has been indicated above, the instant invention, in one aspect, is a dimer of a purpurin, a chlorin or a metal complex with hematoporphyrin or another purpurin, chlorin or metal complex where the dimer has a structure that has been enriched in an atom that can be detected by nuclear magnetic resonance to such an extent that the presence of small amounts of the dimer can be detected by nuclear magnetic resonance. Purpurins having a structure that has been so enriched are produced by repeating the procedure of Example 1, but producing Pyrrole I from a saturated aqueous solution containing one gram equivalent of sodium nitrite enriched in N-15, a 5 percent w/w solution in glacial acetic acid containing one gram equivalent of benzyl propionylacetate, a suspension in glacial acetic acid of one gram equivalent of ethyl acetoacetate and four gram equivalents of zinc dust, and producing Pyrrole III from a saturated aqueous solution containing one gram equivalent of sodium nitrite enriched in N-15, a 5 percent w/w solution in glacial acetic acid containing one gram equivalent of benzyl propionylacetate, a suspension in glacial acetic acid of one gram equivalent of 2,4-pentanedione and four gram equivalents of zinc dust. A 10 percent enrichment of the sodium nitrite in N-15 is adequate to produce Purpurin I, Purpurin II, Purpurin III, Purpurin IV and Purpurin V enriched in N-15 to such an extent that the location of dimers produced therefrom, after they have been administered intravenously as described above, in the patient in whom they were administered can be monitored by nuclear magnetic resonance.

Purpurins having a structure that has been enriched in an atom which can be detected by nuclear magnetic resonance are also produced by repeating Example 1, but producing Porphyrin Complex VII from a solution in 50 ml xylene of 506 mg Porphyrin Complex V and 1.024 g (carbethoxymethylene)triphenylphosphorane in which the carbethoxymethylene moiety is enriched in C-13. A 10 percent enrichment of the carbethoxymethylene moiety in C-13 is adequate to produce Purpurin I, Purpurin II, Purpurin III, Purpurin IV and Purpurin V enriched in C-13 to such an extent that the location of dimers produced therefrom, after they have been administered intravenously as described above, in the patient in whom they were administered can be monitored by nuclear magnetic resonance.

As has also been indicated above, the instant invention, in another aspect, is a dimer of a purpurin, a chlorin or a metal complex with hematoporphyrin or another purpurin, chlorin or metal complex where the dimer has a structure that has been enriched in an atom that is radioactive to such an extent that its presence can be detected by an instrument that measures the level of ionizing radiation. Purpurins having a structure which has been enriched in such an atom are produced by repeating the procedure of Example 1, but producing Porphyrin Complex VII from a solution in 50 ml xylene of 506 mg Porphyrin Complex V and 1.024 g (carbethoxymethylene)triphenylphosphorane in which the carbethoxymethylene moiety is enriched in C-14. A 10 percent enrichment of the carbethoxymethylene moiety in C-14 is adequate to produce Purpurin I, Purpurin II, Purpurin III, Purpurin IV and Purpurin V enriched in C-14 to such an extent that the location of dimers produced therefrom, after they have been administered intravenously as described above, in the patient in whom they were administered can be monitored by an instrument which measures the level of ionizing radiation. It will be appreciated that, because C-14 has an extremely long half life, a dimer of a purpurin, chlorin or complex that has a structure which is enriched in C-14 should not be administered to a human, but that such a compound can be administered to a laboratory animal and that monitoring its location in the body of the laboratory animal can then provide extremely valuable information which has application in the treatment of humans.

Purpurins, chlorins and complexes having structures which are enriched in an atom that emits ionizing radiation and which are suitable for administration to humans can also be produced. For example, any of the purpurins according to the invention where at least one of R10 through R14 is hydrogen can be reacted in sunlight with elemental I-131 or with $^{131}$ICl, and chlorins, complexes and dimers can be produced as described above from the iodinated purpurin which is produced. Further, purpurin and chlorin complexes can be produced as described above from a gallium or molybdenum chelate of pentane, 2,4-dione where the gallium is Ga-67, or the molybdenum is Mo-99. Mo-99 becomes Tc-99m, which, like Ga-67 and I-131, is physiologically acceptable for use as a tracer in human patients. Accordingly, dimers according to the instant invention produced from such compounds containing I-131 and the Ga-67 and Tc-99m complexes are suitable for administration to humans.

It will be appreciated that Purpurins I through V produced as described above, and enriched in N-15, in C-13, in C-14, in I-131 or in Tc-99 m can be used as also described above to produce other purpurins which are so enriched and that the methods of the examples hereof can be varied as described above to produce purpurins having the structures of FIGS. 7, 9–18, 29–33 and 34–38 which are enriched in N-15, in C-13, in C-14, in I-131 or in Tc-99M and wherein each of R1 through R8 has the meaning set forth above. Similarly, the method described above can be used to produce purpurins that are so enriched where each of R9 through R16 has the meaning set forth above. Likewise, chlorins and purpurin metal complexes can be produced from those purpurins as described above, the metal complexes can be produced from the chlorins as so described. Finally, dimers can be produced from the chlorins, purpurins and metal complexes by the method of Example 1 and, when there is a $CO_2CH_3$ or the like group, by the method of Example 2; amines can be produced from the chlorins, purpurins and metal complexes by the method of the first paragraph of Example 3; and dimers can be produced from the amines by the methods of the second paragraph of Example 3 and of Example 4.

As is indicated above, there are indications that the purpurins, chlorins and metal complexes are X ray sensitizers which increase the therapeutic ratio of X rays. Accordingly, in one aspect, the instant invention involves administering, for example, as described above, a dimer of a purpurin having the structure of one of FIGS. 7, 9–18 and 29–38, a dimer of a corresponding chlorin or a dimer of a chlorin or purpurin metal complex and, after the dimer has localized, treating the affected region with X rays or other ionizing radiation.

As is also indicated above, the dimers of purpurins, chlorins and complexes can be administered topically, for example as dilute, e.g., 1 percent w/w solutions in DMSO or ethanol to non-malignant lesions, e.g., of the vagina or bladder, or to such cutaneous lesions as are involved in psoriasis, followed by illumination of the area involved with light of a wavelength at which the dimer has an absorbance peak. The dimer solution should be applied only to the lesions to prevent damage to healty tissue adjacent the lesions. Illumination of the lesions, for example, for from 15 to 30 minutes then completes the treatment. It is to be understood, however, that dimers of purpurins, chlorins and complexes according to the invention can also be administered systemically in the treatment of non-malignant lesions.

The reaction of a monoclonal antibody with a dimer of Purpurin II and Purpurin Alcohol II is described in Example 5. The monoclonal antibody, when it is one which localizes in tumors, can enhance the ability of a dimer of the purpurin, or of a chlorin or complex, to localize in tumors, as discussed above. However, the monoclonal antibody can also be of a different type, for example one which localizes in a particular kind of lymphocyte, in a leukemia cell, in a lymphoma cell, or the like; a dimer of a product of the reaction of Purpurin II or the like with such an antibody which localizes in a particular kind of lymphocyte can be used to modulate lymphocyte populations in the treatment of immune diseases, e.g., arthritis, or to re-establish a lymphocyte balance in transplant patients. Some of the blood is removed from the patient's body, and a dimer of such a purpurin, chlorin or complex according to the invention, i.e., one where at least one of the substituents is a monoclonal antibody directed against the lymphocyte or lymphocytes present in excess, is mixed with the blood in a suitable amount; after the purpurin or the like localizes in the lymphocyte or lymphocytes present in excess, the blood is exposed to light of a wave length at which the dimer has an absorbance peak, destroying the lymphocyte or lymphocytes where localization had occurred. The blood is then returned to the patient's body. This technique can be carried out repeatedly as required to modulate lymphocyte populations in treating immune diseases and transplant patients who develop the lymphocyte imbalance that is associated with the rejection of a transplanted organ. Since the treatment is entirely outside the patient's body, there is no opportunity for the development of a natural resistance to the treatment which is characteristic of prior attempts to modulate lymphocyte populations. Dimers according to the invention where one of the substituents is an antibody against leukemia cells or against lymphoma cells can be used in a similar manner in the treatment of leukemia and lymphoma.

It will be appreciated that dimers of purpurins and chlorins according to the invention where R10 through R13 and R16 are hydrogen are preferred, other factors being equal, because the production of the compounds with other groups in these positions is complicated, time consuming and expensive. R9 and R15, in purpurins, chlorins and complexes from which dimers according to the invention are produced, are preferably $CO_2R'$ where R' is a primary or secondary alkyl group having from 1 to 4 carbon atoms, other factors being equal, because these groups are present at the end of the ring closure reaction which produces the purpurins (see Examples 1 and 6) and because these groups react in the procedures of Examples 1–4 to produce ester and amide dimers. However, the esters of these R9 and R15 substituents can be reduced to formyl groups and reacted as discussed above to introduce any of the R1 to R8, R10 to R14 and R16 substituents if a different reaction is used to produce the desired dimer.

The production of purpurin solutions in the specific non-ionic solubilizer that is available under the designation CREMOPHOR EL, and the production of emulsions of such solutions with 1,2-propanediol and saline solution is described above, as is the use of such solutions to detect and treat tumors. It will be appreciated that dimers according to the invention of purpurins, chlorins and their metal complexes can be dissolved in CREMOPHOR EL or in other non-ionic solubilizers and that the solutions can be used to produce emulsions that can be administered intravenously. For example, other reaction products of ethylene oxide and castor oil can be so used, as can reaction products of ethylene, propylene and other similar oxides with other fatty acids and the reaction products of propylene and other similar oxides with castor oil. Similarly, glycols other than 1,2-propanediol can be used in producing the emulsions for intravenous administration, or the glycol can be omitted, particularly if the solubilizer is prepared to have a lower viscosity and greater compatibility with water, by comparison with the solubilizer that is available under the designation CREMOPHOR EL. It is necessary only that the solution or emulsion be one which is physiologically acceptable and of a suitable concentration, or dilutable to a suitable concentration, for intravenous administration. An indefinitely large number of such solutions and emulsions will be apparent to those skilled in the relevant art from the foregoing specific disclosure. Similarly, the aqueous phase need not be 0.9 percent w/w or any other concentration of sodium chloride. Such saline is presently favored for intravenous administration, but other aqueous phases can also be used, so long as the entire composition is physiologically acceptable for intravenous administration and, in fact, other aqueous phases may subsequently be favored Dosages of 4 and 10 mg per kg of body weight were used in the in vivo procedures described above. It has not been determined that 4 mg per kg is the minimum dosage or that 10 mg per kg is the maximum. Both dosages caused the biological consequences described above. It will be appreciated, therefore, that it is necessary only to use an effective amount of a dimer of a purpurin, chlorin or complex according to the invention in the detection and treatment of tumors, preferably as small a dosage as possible, and that the exact dosage can be determined by routine experimentation. Both systemic administration, specifically intravenous, and local administration, i.e., as a solution in dimethyl sulfoxide or ethanol, have been described above; however, it will also be appreciated that other methods of administration will be suitable, at least in some instances.

Illumination of tumors containing a dimer of a purpurin, a chlorin or a metal complex in accordance with the instant invention can be a surface illumination with a conventional light source, as described above, or can be a surface illumination with a laser. The illumination can also be into the body of a tumor, for example through optical fibers inserted thereinto.

Various changes and modification can be made from the specific details of the invention as described above without departing from the spirit and scope thereof as defined in the appended claims.

We claim:

1. A dimer of (1) a purpurin or a purpurin metal complex having the structure of any of FIGS. 1, 7, 14–18, 29–38, 44–48 or 54–58 of the attached drawings, or a chlorin or a chlorin metal complex having the structure of any of FIGS. 2, 8, 19–28, 39–43 or 49–53 of the attached drawings and (2) hematoporphyrin or a purpurin or a purpurin metal complex having the structure of any of FIGS. 1, 7, 14–18, 29–38, 44–48 or 54–58 of the attached drawings, or a chlorin or a chlorin metal complex having the structure of any of FIGS. 2, 8, 19-28, 39-43 or 49-53 of the attached drawings, wherein each of R10 through R13 and R16 is hydrogen, and each of R1 through R9, R14 and R15 is:

H or CHO, an alkyl group having from 1 to 4 carbon atoms, excluding tertiary butyl, an alkylene group having from 2 to 4 carbon atoms, a group having the formula $R_2N(R_3)_2$ where $R_2$ is a bivalent aliphatic hydrocarbon radical having from 1 to 4 carbon atoms, wherein any carbon to carbon bond is either a single or a double bond, and not more than one is a double bond; $R_3$ is hydrogen or an alkyl group having from 1 to 2 carbon atoms and the two $R_3$ groups can be the same or different, a group having the formula $R_2N(R_4)_3A$ where $R_2$ is a bivalent aliphatic hydrocarbon radical having from 1 to 4 carbon atoms, wherein any carbon to carbon bond is either a single or a double bond, and not more than one is a double bond; A is a physiologically acceptable anion; and $R_4$ is an alkyl group having from 1 to 2 carbon atoms and the three $R_4$ groups can be the same or different, a group having the formula $R_2OH$ were $R_2$ is a bivalent aliphatic hydrocarbon radical having from 1 to 4 carbon atoms, wherein any carbon to carbon bond is either a single or a double bond, and not more than one is a double bond, $CO_2R'$, $CH_2CO_2R'$ or $CH_2CH_2CO_2R'$, where R' is hydrogen or an alkyl group having from 1 to 4 carbon atoms, excluding tertiary butyl, an amino acid moiety which is attached to the purpurin or chlorin moiety through a carbonyl which is a part of an amide produced by reaction between an amine function of a naturally occurring amino acid and a $CO_2R'$, $CH_2CO_2R'$ or $CH_2CH_2CO_2R'$ group of the purpurin or chlorin, a monoclonal antibody moiety which selectively binds to malignant tumors and is attached to the purpurin or chlorin moiety through a carbonyl which is a part of an amide produced by reaction between an amine funtion of a monoclonal antibody and a $CO_2R'$, $CH_2CO_2R'$ or $CH_2CH_2CO_2R'$ group of the purpurin or chlorin, or in the purpurins and purpurin metal complexes of FIGS. 1, 7 14-18, 34-38 and 54-58 and in the chlorins and chlorin metal complexes of FIGS. 2 and 8 R1 can be a bivalent aliphatic hydrocarbon radical having from 2 to 4 carbon atoms wherein both of the valences of the radical are attached to the same carbon atom thereof and to a carbon atom of the purpurin, chlorin, or metal complex, and in the purpurins and purpurin metal complexes of FIGS. 29-33 and of FIGS. 44-48 and in the chlorins and chlorin metal complexes of FIGS. 19-28, 39-43 and 49-53, both R1 and R2 can be bivalent aliphatic hydrocarbon radicals having from 2 to 4 carbon atoms wherein both of the valences of the radical are attached to the same carbon atom thereof and to a carbon atom of the purpurin or metal complex, and M comprises a metal cation that is complexed with two of the nitrogens of the purpurin or chlorin and is Ag, Al, Ce, Co, Cr, Dy, Er, Eu, Fe, Ga, Gd, Hf, Ho, In, La, Lu, Mn, MO, Nd, Pb, Pd, Pr, Pt, Rh, Sb, Sc, Sm, Sn, Tb, Th, Ti, Tl, Tm, U, V, Y, Yb, Zn or Zr, said dimer being the product of reaction between a $CO_2R'$, $CH_2CO_2R'$ or $CH_2CH_2CO_2R'$ group of the (1) purpurin, chlorin or metal complex or of the (2) hematoporphyrin, purpurin, chlorin or metal complex and an amino nitrogen or an alcoholic OH group of the other, with the proviso that not more than one of R1 through R9, R14 and R15 is CHO, a group having the formula $R_2N(R_3)_2$, a group having the formula $R_2N(R_4)_3A$, an amino acid moiety or a monoclonal antibody moiety.

2. As a composition of matter, a dimer of a purpurin, a chlorin or a metal complex as claimed in 1 wherein one of R1 through R9, R14 and R15 is said monoclonal antibody moiety.

3. A composition of matter as claimed in claim 1 wherein one of R1 through R9, R14 and R15 is said moiety of a naturally occurring amino acid.

* * * * *